United States Patent [19]

Hall et al.

[11] Patent Number: 5,504,200
[45] Date of Patent: Apr. 2, 1996

[54] PLANT GENE EXPRESSION

[75] Inventors: Timothy C. Hall; John D. Kemp; Jerry L. Slightom, all of Madison; Dennis W. Sutton, McFarland, all of Wis.; Norimoto Murai, Yatabe, Japan

[73] Assignee: Mycogen Plant Science, Inc., San Diego, Calif.

[21] Appl. No.: 198,673

[22] Filed: Feb. 18, 1994

Related U.S. Application Data

[63] Continuation of Ser. No. 942,100, Sep. 8, 1992, abandoned, which is a continuation of Ser. No. 68,805, Jun. 30, 1987, abandoned, which is a continuation of Ser. No. 617,947, Jun. 6, 1984, abandoned, which is a continuation-in-part of Ser. No. 485,613, Apr. 15, 1983, abandoned.

[51] Int. Cl.$^6$ .......................... C12N 15/29; C12N 15/84; C12N 5/04; A01H 5/00
[52] U.S. Cl. .................. 536/24.1; 435/69.1; 435/70.1; 435/172.3; 435/240.4; 435/252.2; 435/252.3; 435/252.33; 435/320.1; 536/23.6; 800/205; 800/255
[58] Field of Search .................. 435/69.1, 70.1, 435/172.3, 240.4, 252.2, 252.3, 252.33, 320.1; 536/23.6, 24.1; 800/205, 250, 255

[56] References Cited

U.S. PATENT DOCUMENTS

| | | | |
|---|---|---|---|
| 4,418,149 | 11/1983 | Ptashne et al. | 435/253 |
| 4,536,475 | 8/1985 | Anderson | 435/172.3 |
| 5,034,322 | 7/1991 | Rogers et al. | 435/172.3 |

FOREIGN PATENT DOCUMENTS

| | | | |
|---|---|---|---|
| 0099255 | 1/1984 | European Pat. Off. | C12N 15/00 |

OTHER PUBLICATIONS

Schell et al. (1983) Bio/technology 1:175–180.
Gasser et al. 1989. Science 244: 1293–1299.
Matzke et al., Journal of Molecular and Applied Genetics 1 pp. 39–49 (1981).
Hess, "Cell Modification by DNA Uptake". in, Plant Cell, Tissue and Organ Culture ed. Reinert et al., 1977, pp. 506–531.
Herrera–Estrella et al. 1983 Nature 303: 209–213.
Goodman et al. 1987. Science 236:48–54.
Marx, J. 1983. Science 219: 829–830.
Barton et al. 1983. Cell 32: 1033–1043.
Sun et al. 1981. Nature 289: 37–41.
Phillips, R. 1983. Genetic engineering of plants (Basic Life Sciences) 26: 453–465, Kosuge et al., eds., Plenum Press: New York.
Depicker et al. 1982. J. Mol. Appl. Genet. 1(6): 561–573.
van Mantagu et al. 1979 pp. 71–95 In: Plasmids of medical, environmental and commercial importance.
Timmis et al., eds., Elsevier/North–Holland Biomedical Press.
Oliver et al. 1985. p. 44 In: A dictionary of genetic engineering, Cambridge University Press.
Ohen et al. 1981. Mol. Gen. Genet. 183: 209–213.
Gamborg, "Somatic Cell Hybridization by Protoplast Fusion and Morphogenesis" Plant Tissue Culture and its Bio–Technological Application, ed. Barz et al. pp. 287–301 (1977).
Hernalsteens et al., "The Agrobacterium Tumefaciens Ti Plasmid as a Host Vector System for Introducing Foreign DNA" Nature 287 pp. 654–656 (1980).
Marx, "A Transposable Element of Maize Emerges" Science 219 pp. 829–830 (1983).
Barton et al., "Regeneration of Intact Tobacco Plants Containing Full Length Coppies of Genetically Engineered T–DNA" Cell 32 pp. 1033–1043 (1983).

(List continued on next page.)

Primary Examiner—David T. Fox
Attorney, Agent, or Firm—Saliwanchik & Saliwanchik

[57] ABSTRACT

The phaseolin structural gene and promoter are disposed. Also disclosed are plasmids, bacteria, plant cells, plant tissue and plants containing the phaseolin promoter. The promoter finds use in the expression of heterologous plants genes, including the phaseolin gene, in transformed plant cells and plants.

30 Claims, 20 Drawing Sheets

OTHER PUBLICATIONS

Bevan et al., "T–DNA of the Agrobacterium Ti and Ri Plasmids" Annual Review of Genetics 16 pp. 357–384 (1982).

Ream et al., "Crown Gall Disease and Prospects for Genetic Manipulation of Plants" Science 218 pp. 854–859 (1982).

Sun et al., "Intervening Sequences in Plant Gene–Comparison of the Partial Sequence of cDNA and Genomic DNA of French Bean Phaseolin" Nature 289 pp. 37–41 (1981).

Slightom et al., "Complete Nucleotide Sequence of a French Bean Storage Protein Gene Phaseolin" Proceedings of the National Academy of Sciences 80 pp. 1897–1901 (1983).

Gelvin et al., "Sizes and Map Positions of Several Plasmid DNA Encoded Transcripts in Octopine Type Crown Gall Tumors" Proceedings of the National Academy of Sciences 79 pp. 76–80 (1982).

Holsters et al., "Sizes and Map Positions of Several Plasmid DNA Encoded The Use of Selectable Markers . . . " Molecular and General Genetics 185 pp. 283–289 (1982).

Garfinkel et al., "Genetic Analysis of Crown Gall: Fine Structure Map of the T–DNA by site–Directed Mutagenesis" Cell 27 pp. 143–153 (1981).

DeGreve et al., "Regeneration of Normal and Fertile Plants that Express Octopine Synthase, From Tobacco Crown Galls" Nature 300 pp. 752–755 (1982).

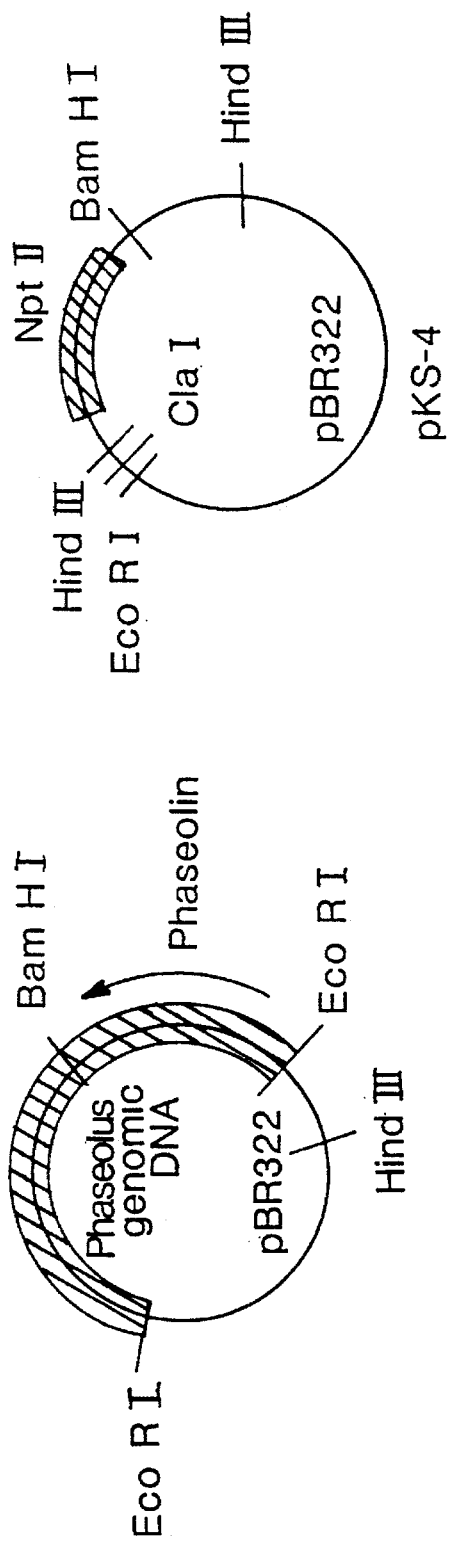
FIG. 15
FIG. 16
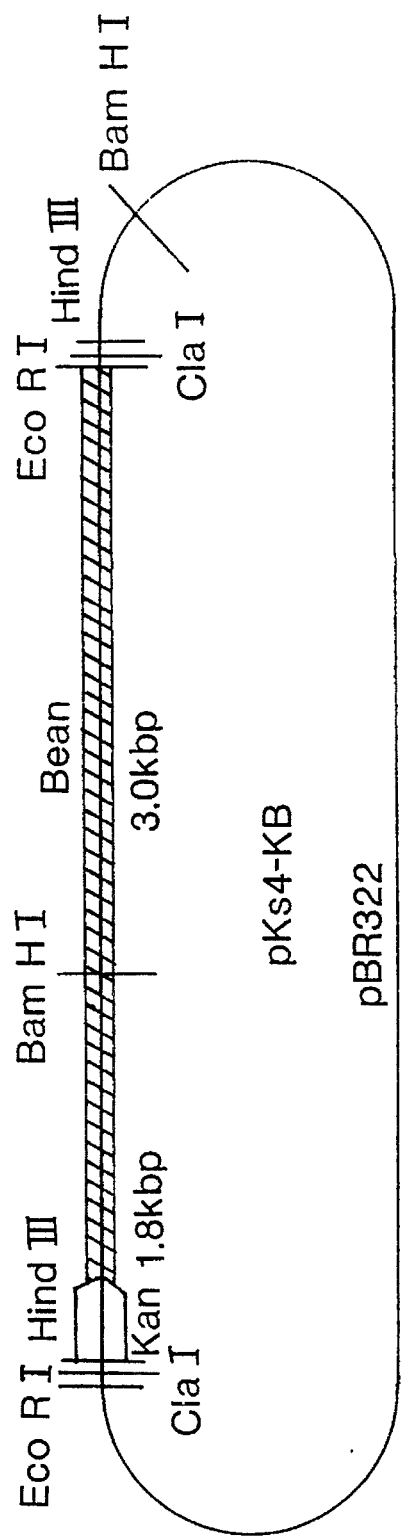
FIG. 17

PLANT GENE EXPRESSION

This application is a continuation, of application Ser. No. 07/942,100, filed Sep. 8, 1992, now abandoned, which is a continuation of application Ser. No. 07/068,805, filed Jun. 30, 1987, now abandoned, which is a continuation of application Ser. No. 06/617,947, filed Jun. 6, 1984, now abandoned, which is a continuation-in-part of application Ser. No. 06/485,613, filed Apr. 15, 1983, now abandoned.

BACKGROUND AND FIELD OF THE INVENTION

Shuttle Vectors

Shuttle vectors, developed by Ruvkun and Ausubel (1981) Nature 289:85–88, provide a way to insert foreign genetic materials into positions of choice in a large plasmid, virus, or genome. There are two main problems encountered when dealing with large plasmids or genomes. Firstly, the large plasmids may have many sites for each restriction enzyme. Unique, site-specific cleavage reactions are not reproducible and multi-site cleavage reactions followed by ligation lead to great difficulties due to the scrambling of the many fragments whose order and orientation one does not want changed. Secondly, the transformation efficiency with large DNA plasmids is very low. Shuttle vectors allow one to overcome these difficulties by facilitating the insertion, often in vitro, of the foreign genetic material into a smaller plasmid, then transferring, usually by in vivo techniques, to the larger plasmid.

A shuttle vector consists of a DNA molecule, usually a plasmid, capable of being introduced into the ultimate recipient bacteria. It also includes a copy of the fragment of the recipient genome into which the foreign genetic material is to be inserted and a DNA segment coding for a selectable trait, which is also inserted into the recipient genome fragment. The selectable trait ("marker") is conveniently inserted by transposon mutagenesis or by restriction enzymes and ligases.

The shuttle vector can be introduced into the ultimate recipient cell typically a bacterium of the genus Agrobacterium by a tri-parental mating (Ruvkun and Ausubel, supra), direct transfer of a self-mobilizable vector in a bi-parental mating, direct uptake of exogenous DNA by Agrobacterium cells ("transformation", using the conditions of M. Holsters et al. (1978) Molec. Gen. Genet. 163:181–187), by spheroplast fusion of Agrobacterium with another bacterial cell, by uptake of liposome-encapsulated DNA, or infection with a shuttle vector that is based on a virus that is capable of being packaged in vitro. A tri-parental mating involves the mating of a strain containing a mobilizable plasmid, which carries genes for plasmid mobilization and conjugative transfer, with the strain containing the shuttle vector. If the shuttle vector is capable of being mobilized by the plasmid genes, the shuttle vector is transferred to the recipient cell containing the large genome, e.g. the Ti or Ri plasmids of Agrobacterium strains.

After the shuttle vector is introduced into the recipient cell, possible events include a double cross over with one recombinational event on either side of the marker. This event will result in transfer of a DNA segment containing the marker to the recipient genome replacing a homologous segment lacking the insert. To select for cells that have lost the original shuttle vector, the shuttle vector must be incapable of replicating in the ultimate host cell or be incompatible with an independently selectable plasmid pre-existing in the recipient cell. One common means of arranging this is to provide in the third parent another plasmid which is incompatible with the shuttle vector and which carries a different drug resistance marker. Therefore, when one selects for resistance to both drugs, the only surviving cells are those in which the marker on the shuttle vector has recombined with the recipient genome. If the shuttle vector carries an extra marker, one can then screen for and discard cells that are the result of a single cross-over between the shuttle vector and the recipient plasmid resulting in cointegrates in which the entire shuttle vector is integrated with the recipient plasmid. If the foreign genetic material is inserted into or adjacent to the marker that is selected for, it will also be integrated into the recipient plasmid as a result of the same double recombination. It might also be carried along when inserted into the homologous fragment at a spot not within or adjacent to the marker, but the greater the distance separating the foreign genetic material from the marker, the more likely will be a recombinational event occurring between the foreign genetic material and marker, preventing transfer of the foreign genetic material.

Shuttle vectors have proved useful in manipulation of Agrobacterium plasmids: see D. J. Garfinkel et al. (1981) Cell 27:143–153, A. J. M. Matzke and M. D. Chilton (1981) J. Molec. Appl. Genet. 1:39–49, and J. Leemans et al. (1981) J. Molec. Appl. Genet. 1:149–164, who referred to shuttle vectors by the term "intermediate vectors".

Agrobacterium-Overview

Included within the gram-negative bacterial family Rhizobiaceae in the genus Agrobacterium are the species *A. tumefaciens* and *A. rhizogenes*. These species are respectively the causal agents of crown gall disease and hairy root disease of plants. Crown gall is characterized by the growth of a gall of dedifferentiated tissue. Hairy root is a teratoma characterized by inappropriate induction of roots in infected tissue. In both diseases, the inappropriately growing plant tisssue usually produces one or more amino acid derivatives, known as opines, not normally produced by the plant which are catabolized by the infecting bacteria. Known opines have been classified into three families whose type members are octopine, nopaline, and agropine. The cells of inappropriately growing tissues can be grown in culture, and, under appropriate conditions, be regenerated into whole plants that retain certain transformed phenotypes.

Virulent strains of Agrobacterium harbor large plasmids known as Ti (tumor-inducing) plasmids in *A. tumefaciens* and Ri (root-inducing) plasmids in *A. rhizogenes*. Curing a strain of these plasmids results in a loss of pathogenicity. The Ti plasmid contains a region, referred to as T-DNA (transferred-DNA), which in tumors is found to be integrated into the genome of the host plant. The T-DNA encodes several transcripts. Mutational studies have shown that some of these are involved in induction of tumorous growth. Mutants in the genes for tml, tmr, and tms, respectively result in large tumors (in tobacco), a propensity to generate roots, and a tendency for shoot induction. The T-DNA also encodes the gene for at least one opine synthetase, and the Ti plasmids are often classified by the opine which they caused to be synthesized. Each of the T-DNA genes is under control of a T-DNA promoter. The T-DNA promoters resemble eukaryotic promoters in structure, and they appear to function only in the transformed plant cell. The Ti plasmid also carries genes outside the T-DNA region. These genes are involved in functions which include opine catabolism, oncogenicity, agrocin sensitivity, replication, and autotransfer to bacterial cells. The Ri plasmid is organized in a fashion analogous to the Ti plasmid. The set of genes and DNA sequences responsible for transforming the plant cell are hereinafter collectively referred to as the transformation-inducing principle (TIP). The designation TIP therefore includes both Ti and Ri plasmids. The integrated segment of a TIP is termed herein "T-DNA", whether derived from a Ti plasmid or an Ri plasmid. Recent general reviews of Agrobacterium-caused disease include those by D. J. Merlo (1982), Adv. Plant Pathol. 1:139–178 L. W. Ream and M. P. Gordon (1982), Science 218:854–859, and M. W. Bevan and M. D. Chilton (1982), Ann. Rev. Genet. 166:357–384; G. Kahl and J. Schell (1982) *Molecular Biology of Plant Tumors.*

Agrobacterium-Infection of Plant Tissues

Plant cells can be transformed in by Agrobacterium a number of methods known in the art which include but are not limited to co-cultivation of plant cells in culture with Agrobacterium, direct infection of a plant, fusion of plant protoplasts with Agrobacterium spheroplasts, direct transformation by uptake of free DNA by plant cell protoplasts, transformation of protoplasts having partly regenerated cell walls with intact bacteria, transformation of protoplasts by liposomes containing T-DNA, use of a virus to carry in the T-DNA, microinjection, and the like. Any method will suffice as long as the gene is reliably expressed, and is stably transmitted through mitosis and meiosis.

The infection of plant tissue by Agrobacterium is a simple technique well known to those skilled in the art (for an example, see D. N. Butcher et al. (1980) in *Tissue Culture Methods for Plant Pathologists*, eds.: D. S. Ingrams and J. P. Helgeson, pp. 203–208). Typically a plant is wounded by any of a number of ways, which include cutting with a razor, puncturing with a needle, or rubbing with abrasive. The wound is then inoculated with a solution containing tumor-inducing bacteria. An alternative to the infection of intact plants is the inoculation of pieces of tissues such as potato tuber disks (D. K. Anand and G. T. Heberlein (1977) Amer. J. Bot. 64:153–158) or segments of tobacco stems (Binns, et al.). After induction, the tumors can be placed in tissue culture on media lacking phytohormones. Hormone independent growth is typical of transformed plant tissue and is in great contrast to the usual conditions of growth of such tissue in culture (A. C. Braun (1956) Cancer Res. 16:53–56).

Agrobacterium is also capable of infecting isolated cells and cells grown in culture, Marton et al. (1979) Nature 277:129–131, and isolated tobacco mesophyll protoplasts. In the latter technique, after allowing time for partial regeneration of new cell walls, Agrobacterium cells were added to the culture for a time and then killed by the addition of antibiotics. Only those cells exposed to *A. tumefaciens* cells harboring the Ti plasmid were capable of forming calli when plated on media lacking hormone. Most calli were found to contain an enzymatic activity involved in opine anabolism. Other workers (R. B. Horsch and R. T. Fraley (18 Jan. 1983) 15th Miami Winter Symposium) have reported transformations by co-cultivation, leading to a high rate (greater than 10%) of calli displaying hormone-independent growth, with 95% of those calli making opines. M. R. Davey et al. (1980) in Ingram and Helgeson, supra, pp. 209–219, describe the infection of older cells that had been regenerated from protoplasts.

Plant protoplasts can be transformed by the direct uptake of TIP plasmids. M. R. Davey et al. (1980) Plant Sci. Lett. 18:307–313, and M. R. Davey et al. (1980) in Ingram and Helgeson, supra, were able to transform Petunia protoplasts with the Ti plasmid in the presence of poly-L-and ornithine to a phenotype of opine synthesis and hormone-independent growth in culture. It was later shown (J. Draper et al. (1982) Plant and Cell Physiol. 23:451–458, M. R. Davey et al. (1982) in *Plant Tissue Culture 1982*, ed: A. Fujiwara, pp. 515–516) that polyethelene glycol stimulated Ti uptake and that some T-DNA sequences were integrated into the genome. F. A. Krens et al. (1982) Nature 296:72–74, reported similar results using polyethelene glycol following by a calcium shock, though their data suggests that the integrated T-DNA included flanking Ti plamid sequences.

An alternative method to obtain DNA uptake involves the use of liposomes. The preparation of DNA containing liposomes is taught by Papahadjopoulos in U.S. Pat. Nos. 4,078,052 and 4,235,871. Preparations for the introduction of Ti-DNA via liposomes have been reported (T. Nagata et al. (1982) in Fujiwara, supra, pp. 509–510, and T. Nagata (1981) Mol. Gen. Genet. 184:161–165). An analogous system involves the fusion of plant and bacterial cells after removal of their cell walls. An example of this technique is the transformation of Vinca protoplast by Agrobacterium spheroplasts reported by S. Hasezawa et al. (1981) Mol. Gen. Genet. 182:206–210. Plant protoplasts can take up cell wall delimited Agrobacterium cells (S. Hasezawa et al. (1982) in Fujiwara, supra pp. 517–518).

T-DNA can be transmitted to tissue regenerated from a fusion of two protoplasts, only one of which had been transformed (G. J. Wullems et al. (1980) Theor. Appl. Genet. 56:203–208). As detailed in the section on Regeneration of Plants, T-DNA can pass through meiosis and be transmitted to progeny as a simple Mendelian trait.

Agrobacterium-Regeneration of Plants

Differentiated plant tissues with normal morphology have been obtained from crown gall tumors. A. C. Braun and H. N. Wood (1976) Proc. Natl. Acad. Sci. USA 73:496–500, grafted tobacco teratomas onto normal plants and were able to obtain normally appearing shoots which could flower. The shoots retained the ability to make opines and to grow independently of phytohormones when placed in culture. In the plants screened, these tumor phenotypes were not observed to be transmitted to progeny, apparently being lost during meiosis (R. Turgeon et al. (1976) Proc. Natl. Acad. Sci. USA 73:3562–3564). Plants which had spontaneouly lost tumorous properties, or which were derived from teratoma seed, were initially shown to have lost all their T-DNA (F.-M. Yang et al. (1980) In Vitro 16:87–92, F. Yang et al. (1980) Molec. Gen. Genet. 177:707–714, M. Lemmers et al. (1980) J. Mol. Biol. 144:353–376). However, later work with plants that had become revertants after hormone treatment (1 mg/l kinetin) showed that plants which had gone through meiosis, though losing T-DNA genes responsible for the transformed phenotype, could retain sequences homologous to both ends of T-DNA (F. Yang and R. B. Simpson (1981) Proc. Natl. Acad. Sci. USA 78:4151–4155). G. J. Wullems et al. (1981) Cell 24:719–724, further demonstrated that genes involved in opine anabolism were capable of passing through meiosis though the plants were male sterile and that seemingly unaltered T-DNA could be inherited in a Mendelian fashion (G. Wullems et al. (1982) in A. Fujiwara, supra). L. Otten et al. (1981) Molec. Gen. Genet. 183:209–213, used Tn7 transposon-generated Ti plasmid mutants in the tms (shoot-inducing) locus to create tumors which proliferated shoots. When these shoots were regenerated into plants, they were found to form self-fertile flowers. The resultant seeds germinated into plants which contained T-DNA and made opines. Similar experiments with a tmr (root-inducing) mutant showed that full-length T-DNA could be transmitted through meiosis to progeny, that in those progeny nopaline genes could be expressed, though at variable levels, and that cotransformed yeast alcohol dehydrogenase I gene was not expressed (K. A. Barton et al. (1983) Cell 32:1033–1043). It now appears that regenerated tissues which lack T-DNA sequences are probably descended from untransformed cells which "contaminate" the tumor (G. Ooms et al. (1982) Cell 30:589–597).

Roots resulting from transformation from *A. rhizogenes* have proven relatively easy to regenerate into plantlets (M.-D. Chilton et al. (1982) Nature 295:432–434.

Agrobacterium-Genes on the TIP Plasmids

A number of genes have been identified within the T-DNA of the TIP plasmids. About half a dozen octopine plasmid T-DNA transcripts have been mapped (S. B. Gelvin et al. (1982) Proc. Natl. Acad. Sci. USA 79:76–80, L. Willmitzer et al. (1982) EMBO J. 1:139–146) and some functions have been assigned (J. Leemans et al. (1982) EMBO J. 1:147–152). The four genes of an octopine type plasmid that have been well defined by transposon mutagenesis include tms, tmr, and tml (D. J. Garfinkel et al. (1981) Cell 27:143–153). Ti plasmids which carry mutations in these genes respectively incite tumorous calli of *Nicotiana tabacum* which generate shoots, proliferate roots, and are larger than normal. In other hosts, mutants of these genes can induce different phenotypes (see Chilton, M. D., Ann. Rev. Genet. (1982). The phenotypes of tms and tmr are correlated with differences in the phytohormone levels present in the tumor. The differences in cytokinin:auxin ratios are similar to those which in culture induce shoot or root formation in untransformed callus tissue (D. E. Akiyoshi et al. (1983) Proc. Natl. Acad. Sci. USA 80:407–411). T-DNA containing a functional gene for either tms or tmr alone, but not functional tml alone, can promote significant tumor growth. Promotion of shoots and roots is respectively stimulated and inhibited by functional tml (L. W. Ream et al. (1983) Proc. Natl. Acad. Sci. USA 80:1660–1664). Mutations in T-DNA genes do not seem to affect the insertion of T-DNA into the plant genome (J. Leemans et al. (1982) supra, L. W. Ream et al. (1983) supra). The ocs gene encodes octopine synthetase, which has been sequenced by H. De Greve et al. (1982) J. Mol. Appl. Genet. 1:499–511. It does not contain introns (intervening sequences commonly found in eukaryotic genes which are posttranscriptionally spliced out of the messenger precursor during maturation of the mRNA). It does have sequences that resemble a eukaryotic transcriptional signal ("TATA box") and a polyadenylation site. As plant cells containing the enzyme octopine synthetase detoxify homo-arginine, the ocs gene may prove to be a useful selectable marker for plant cells that have been transformed by foreign DNA (G. M. S. Van Slogteren et al (1982) Plant Mol. Biol. 1:133–142).

Nopaline Ti plasmids encode the nopaline synthetase gene (nos), which has been sequenced by A. Depicker et al. (1982) J. Mol. Appl. Genet. 1:561–573. As was found with the ocs gene, nos is not interrupted by introns. It has two putative polyadenylation sites and a potential "TATA box". In contrast to ocs, nos is preceeded by a sequence which may be a transcriptional signal known as a "CAT box". J. C. McPhersson et al. (1980) Proc. Natl. Acad. Sci. USA 77:2666–2670, reported the in vitro translation of T-DNA encoded mRNAs from crown gall tissues.

Transcription from hairy root T-DNA has also been detected (L. Willmitzer et al. (1982) Mol. Gen. Genet. 186:16–22). Functionally, the hairy root syndrome appears to be equivalent of a crown gall tumor incited by a Ti plasmid mutated in tmr (F. F. White and E. W. Nester (1980) J. Bacteriol. 144:710–720.

In eukaryotes, methylation (especially of cytosine residues) of DNA is correlated with transcriptional inactivation; genes that are relatively undermethylated are transcribed into mRNA. Gelvin et al. (1983) Nucleic Acids Res. 1:159–174, has found that the T-DNA in crown gall tumors is always present in at least one unmethylated copy. That the same genome may contain numerous other copies of T-DNA which are methylated suggests that the copies of T-DNA in excess of one may be biologically inert. (See also G. Ooms et al. (1982) Cell 30:589–597.)

The Ti plasmid encodes other genes which are outside of the T-DNA region and are necessary for the infection process. (See M. Holsters et al. (1980) Plasmid 3:212–230 for nopaline plasmids, and H. De Greve et al. (1981) Plasmid 6:235–248, D. J. Garfinkel and E. W. Nester (1980) J. Bacteriol 144:732–743, and G. Ooms (1980) J. Bacteriol 144:82–91 for octopine plasmids). Most important are the onc genes, which when mutated result in Ti plasmids incapable of oncogenecity. (These loci are also known as vir, for virulence.) The onc genes function in trans, being capable of causing the transformation of plant cells with T-DNA of a different plasmid type and physically located on another plasmid (J. Hille et al. (1982) Plasmid 7:107–118, H. J. Klee et al. (1982) J. Bacteriol 150:327–331, M.-D. Chilton (18 Jan. 1983) 15th Miami Winter Symp. Nopaline Ti DNA has direct repeats of about 25 base pairs immediately adjacent to the left and right borders of the T-DNA which might be involved in either excision from the Ti plasmid or integration into the host genome (N. S. Yadav et al. (1982) Proc. Natl. Acad. Sci. USA 79:6322–6326), and a homologous sequence has been observed adjacent to an octopine T-DNA border (R. B. Simpson et al. (1982) Cell 29:1005–1014). Opine catabolism is specified by the occ and noc genes, respectively of octopine- and nopaline-type plasmids. The Ti plasmid also encodes functions necessary for its own reproduction including an origin of replication. Ti plasmid transcripts have been detected in *A. tumefaciens* cells by S. B. Gelvin et al. (1981) Plasmid 6:17–29, who found that T-DNA regions were weakly transcribed along with non-T-DNA sequences. Ti plasmid-determined characteristics have been reviewed by Merlo, supra (see especially Table II), and Ream and Gordon supra.

Agrobacterium-TIP Plasmid DNA

Different octopine-type Ti plasmids are nearly 100% homologous to each other when examined by DNA hybridization (T. C. Currier and E. W. Nester (1976) J. Bacteriol. 126:157–165) or restriction enzyme analysis (D. Sciaky et al. (1978) Plasmid 1:238–253). Nopaline-type Ti plasmids have as little as 67% homology to each other (Currier and Nester, supra). A survey revealed that different Ri plasmids are very homologous to each other (P. Costantino et al. (1981) Plasmid 5:170–182). N. H. Drummond and M.-D. Chilton (1978) J. Bacteriol. 136:1178–1183, showed that proportionally small sections of octopine and nopaline type Ti plasmids were homologous to each other. These homologies were mapped in detail by G. Engler et al. (1981) J. Mol.

Biol. 152:183–208. They found that three of the four homologous regions were subdivided into three (overlapping the T-DNA), four (containing some onc genes), and nine (having onc genes) homologous sequences. The uninterrupted homology contains at least one tra gene (for conjugal transfer of the Ti plasmid to other bacterial cells), and genes involved in replication and incompatibility. This uninterrupted region has homology with a Sym plasmid (involved in symbiotic nitrogen fixation) from a species of Rhizobium, a different genus in the family Rhizobiaceae (R. K. Prakash et al. (1982) Plasmid 7:271–280). The order of the four regions is not conserved, though they are all oriented in the same direction. Part of the T-DNA sequence is very highly conserved between nopaline and octopine plasmids (M.-D. Chilton et al. (1978) Nature 275:147–149, A. Depicker et al. (1978) Nature 275:150 153). Ri plasmids have been shown to have extensive homology among themselves, and to both octopine (F. F. White and E. W. Nester (1980) J. Bacteriol. 144:710–720) and nopaline (G. Risuleo et al. (1982) Plasmid 7:45 51) Ti plasmids, primarily in regions encoding onc genes. Ri T-DNA contains extensive though weak homologies to T-DNA from both types of Ti plasmid (L. Willmitzer et al. (1982) Mol. Gen. Genet. 186:3193–3197). Plant DNA from uninfected *Nicotiana glauca* contains sequences, referred to as cT-DNA (cellular T-DNA), that show homology to a portion of the Ri T-DNA (F. F. White et al. (1983) Nature 301:348-350).

It has been shown that a portion of the Ti (M.-D. Chilton et al. (1977) Cell 11:263–271) or Ri (M.-D. Chilton (1982) Nature 295:432–434, F. F. White et al. (1982) Proc. Natl. Acad. Sci. USA 799:3193–3197, L. Willmitzer (1982) Mol. Gen. Genet. 186:16–22) plasmid is found in the DNA of tumorous plant cells. The transferred DNA is known as T-DNA. T-DNA is integrated into the host DNA (M. F. Thomashow et al. (1980) Proc. Natl. Acad. Sci. USA 77:6448–6452, N. S. Yadav et al. (1980) Nature 287:458–461) in the nucleus (M. P. Nuti et al. (1980) Plant Sci. Lett. 18:1–6, L. Willmitzer et al. (1980) Nature 287:359–361, M.-D. Chilton et al. (1980) Proc. Natl. Acad. Sci. USA 77:4060 4064).

M. F. Thomashow et al. (1980) Proc. Natl. Acad. Sci. USA 77:6448–6452, and M. F. Thomashow et al. (1980) Cell 19:729–739, found the T-DNA from octopine-type Ti plasmids to have been integrated in two separate sections, TL-DNA and TR-DNA, left and right T-DNAs respectively. The copy numbers of TR and TL can vary (D. J. Merlo et al. (1980) Molec. Gen. Genet. 177:637–643). A core of T-DNA is highly homologous to nopaline T-DNA (Chilton et al. (1978) supra and Depicker et al. (1978) supra), is required for tumor maintenance, is found in TL, is generally present in one copy per cell, and codes for the genes tms, tmr, and tml. On the other hand TR can be totally dispensed with (M. De Beuckeleer et al. (1981) Molec. Gen. Genet. 183:283–288, G. Ooms et al. (1982) Cell 30:589–597), though found in a high copy number (D. J. Merlo et al. (1980) supra). G. Ooms et al. (1982) Plasmid 7:15–29, hypothesized that TR is involved in T-DNA integration, though they find that when TR is deleted from the Ti plasmid, *A. tumefaciens* does retain some virulence. G. Ooms et al. (1982) Cell 30:589–597, showed that though T-DNA is occasionally deleted after integration in the plant genome, it is generally stable and that tumors containing a mixture of cells that differ in T-DNA organization are the result of multiple transformation events. The ocs is found in TL but can be deleted from the plant genome without loss of phenotypes related to tumorous growth. The left border of integrated TL has been observed to be composed of repeats of T-DNA sequences which are in either direct or inverted orientations (R. B. Simpson et al. (1982) Cell 29:1005–1014).

In contrast to the situation in octopine-type tumors, nopaline T-DNA is integrated into the host genome in one continuous fragment (M. Lemmers et al. (1980) J. Mol. Biol. 144:353–376, P. Zambryski et al. (1980) Science 209:1385–1391). Direct tandem repeats were observed. T-DNA of plants regenerated from teratomas had minor modifications in the border fragments of the inserted DNA (Lemmers et al. supra). Sequence analysis of the junction between the right and left borders revealed a number of direct repeats and one inverted repeat. The latter spanned the junction (Zambryski et al. (1980) supra). The left junction has been shown to vary by at least 70 base pairs while the right junction varies no more than a single nucleotide (P. Zambryski et al. (1982) J. Molec. Appl. Genet. 1:361–370). Left and right borders in junctions of tandem arrays were separated by spacers which could be over 130 bp. The spacers were of unknown origin and contained some T-DNA sequences. T-DNA was found to be integrated into both repeated and low copy number host sequences.

N. S. Yadav et al. (1982) Proc. Natl. Acad. Sci. USA 79:6322–6326, have found a chi site, which in the bacteriophage λ augments general recombination in the surrounding DNA as far as 10 kilobases away, in a nopaline Ti plasmid just outside the left end of the T-DNA. R. B. Simpson et al. (1982) Cell 29:1005–1014, have not observed a chi sequence in an octopine Ti plasmid, though the possible range of action does not eliminate the possibility of one being necessary and present but outside of the region sequenced. The significance of the chi in the Ti plasmid is not known. If the chi has a function, it is probably used in Agrobacterium cells and not in the plants, as chi is not found within the T-DNA.

Agrobacterium-Manipulations of the TIP Plasmids

As detailed in the section on Shuttle Vectors, technology has been developed for the introduction of altered DNA sequences into desired locations on a TIP plasmid. Transposons can be easily inserted using this technology (D. J. Garfinkel et al. (1981) Cell 27:143–153). J.-P. Hernalsteen et al. (1980) Nature 287:654–656, have shown that a DNA sequence (here a bacterial transposon) inserted into T-DNA in the Ti plasmid is transferred and integrated into the recipient plant's genome. Though insertion of foreign DNA has been done with a number of genes from different sources, to date the genes have not been expressed under control of their own promoters. Sources of these genes include alcohol dehydrogenase (Adh) from yeast (K. A. Barton et (1983)), AdhI (J. Bennetzen, unpublished) and zein from corn, interferon and globin from mammals, and the mammalian virus SV40 (J. Schell, unpublished). M. Holsters et al. (1982) Mol. Gen. Genet. 185:283–289, have shown that a bacterial transposon (Tn7) inserted into T-DNA could be recovered in a fully functional and seemingly unchanged form after integration into a plant genome.

Deletions can be generated in a TIP plasmid by several methods. Shuttle vectors can be used to introduce deletions constructed by standard recombinant DNA techniques (Cohen and Boyer U.S. Pat. No. 4,237,224). Deletions with one predetermined end can be created by the improper excision of transposons (B. P. Koekman et al. (1979) Plasmid 2:347–357, G. Ooms et al. (1982) Plasmid 7:15–29). J. Hille and R. Schilperoot (1981) Plasmid 6:151–154, have demonstrated that deletions having both ends at predetermined positions can be generated by use of two transposons. The technique can also be used to construct "recombinant DNA" molecules in vivo.

The nopaline synthetase gene has been used for insertion of DNA segments coding for drug resistance that can be used to select for transformed plant cells. M. Bevan (reported by M. D. Chilton et al. (18 Jan. 1983) 15th Miami Winter Syrup., see also J. L. Marx (1983) Science 219:830) and R. Horsch et al. (18 Jan. 1983) 15th Miami Winter Symp., see Marx, supra, have inserted the kanamycin resistance gene (neomycin phosphotransferase) from Tn5 behind (under control of) the nopaline promoter. The construction was used to transform plant cells which in culture displayed resistance to kanamycin and its analogs such as G418. J. Schell et al. (18 Jan. 1983) 15th Miami Winter Symp. (see also Marx, supra), reported a similar construction, in which the methotrexate resistance gene (dihydrofolate reductase) from Tn7 was placed behind the nopaline synthetase promoter. Transformed cells were resistant to methotrexate. As plant cells containing octopine synthetase are resistant to the toxic chemical homo-arginine, G. M. S. Van Slogteren et al. (1982) Plant Mol. Biol. 1:133–142, have proposed using that enzyme as a selectable marker.

M.-D. Chilton et al. (1983) supra, reported that A. Defremeux has constructed a "mini-Ti plasmid". In the nopaline T-DNA there is normally only one site cut by the restriction enzyme KpnI. A mutant lacking the site was constructed and a KpnI fragment, containing the entire nopaline T-DNA, was isolated. This fragment together with a kanamycin resistance gene was inserted into pRK290, thereby resulting in a plasmid which could be maintained in A. tumefaciens and lacked almost all non-T-DNA Ti sequences. By itself, this plasmid was not able to transform plant cells. However when placed in an A. tumefacien strain containing an octopine Ti plasmid, tumors were induced which synthesized both octopine and nopaline. This indicated that the missing nopaline Ti plasmid functions were complemented by the octopine Ti plasmid, and that the nopaline "mini-Ti" was functional in the transformation of plant cells. Chilton et al. (1983) supra also reported on the construction of a "micro-Ti" plasmid made by resectioning the mini-Ti with SmaI to delete essentially all of T-DNA but the nopaline synthetase gene and the left and right borders. The micro-Ti was inserted into a modified pRK290 plasmid that was missing its Sinai site, and employed in a manner similar to mini-Ti, with comparable results.

H. Lorz et al. (1982) in *Plant Tissue Culture* 1982, ed: A. Fujwara, pp. 511–512, reported the construction of a plasmid vector, apparently independent of the TIP system for DNA uptake and maintenance, that used the nopaine synthetase gene as a marker.

Phaseol in and gene regulation

In general the genes of higher eukaryotes are highly regulated. A multicellular organism, such as a plant, has a number of differentiated tissues, each with its own specialized functions, each of which requires specialized gene products. One such tissue is the cotyledon. In legumes, the cotyedons usually serve as the storage tissue for the seed, holding reserves of lipid, carbohydrate, minerals, and protein until the seed neeeds them during germination. In *Phaseolus vulgaris* L. (also known as the French bean, kidney bean, navy bean, green bean and other names), the major storage protein is known as phaseolin. This protein comprises a small number of molecular species that are extremely homologous and equivalent to one another. Phaseolin contributes most of the nutrition value of dried beans, often comprising more than 10% of the weight of a dried bean.

Phaseolin is highly regulated during the life cycle of *P. vulgaris*. The protein is made essentially only while seed is developing within the pod. Levels rise from the limit of detection to as much as half the seed's protein content, following genetically determined schedules for synthesis. At its peak, phaseol in synthesis can account for over 80% of a cotyledon cell's protein synthesis. At other times and in other tissues, phaseolin synthesis is undetectable. The extreme nature of phaseolin's regulation, coupled with its worldwide nutritional importance, has lead to much interest in the study of phaseolin, its properties, and its regulation.

SUMMARY OF THE INVENTION

The invention disclosed herein provides a plant comprising a genetically modified plant cell having a plant gene introduced and expressed therein. Further, the invention includes plant tissue comprising a plant cell whose genome includes T-DNA comprising a plant gene, said plant gene being expressible in the plant cell. Also provided are novel strains of bacteria of the genus Agrobacterium containing and replicating T-DNA, as defined herein, the T-DNA being modified to contain an inserted plant gene expressible in a plant cell. Further, the invention provides novel plasmids having the ability to replicate in *E. coli* and comprising T-DNA, and further comprising a plant gene inserted within T-DNA contained within the plasmid.

The experimental work disclosed herein is believed to be the first demonstration that plant genes are expresssible in plant cells after introduction via T-DNA, that is to say, by inserting the plant genes into T-DNA and introducing the T-DNA containing the insert into a plant cell using known means. The disclosed experiments are also believed to provide the first demonstration that plant genes containing introns are expressed in plant cells after introduction via T-DNA. These results are suprising in view of the fact that all genes previously known to be expressible in T-DNA, either endogenous T-DNA genes or inserted foreign genes, lacked introns so far as is presently known. The results are unexpected also in view of the fact that the art has never previously been able to demonstrate that a promoter exogenous to the genes of T-DNA could function to control expression in a plant when introduced into T-DNA.

The invention is useful for genetically modifying plant tissues and whole plants by introducing useful plant genes from other plant species or strains. Such useful plant genes include, but are not limited to, genes coding for storage proteins, lectins, resistance factors against disease, insects and herbicides, factors providing tolerance to environmental stress, genes for specific flavor elements, and the like. The invention is exemplified by the introduction and expression of phaseolin, a major seed storage protein of beans, into sunflower and tobacco plant tissues. Once plant cells expressing a plant gene introduced via T-DNA are obtained, plant tissues and whole plants can be regenerated therefrom by means of methods known in the art. The regenerated plants are then reproduced by conventional means and the introduced genes can be transferred to other strains by conventional plant breeding techniques. The introduction and expression of the phaseolin gene, for example, can be used to enhance the protein content and nutritional value of forage crops such as alfalfa. Other uses of the invention, exploiting the properties of other genes, introduced into other plant species, will be readily apparent to those skilled in the art. The invention in principle applies to any introduction of plant genes into any plant species into which T-DNA can be introduced and in which T-DNA can remain stably replicated. In general these species include, but are not limited to, dicotyledonous plants, such as sunflower (family Compositeae), tobacco (family Solanaceae), alfalfa, soybeans and other legumes (family Leguminoseae) and most vegetables.

BRIEF DESCRIPTION OF THE DRAWINGS

FIG. 15 depicts plasmid construct p7.2.

FIG. 16 depicts plasmid construct pKS-4.

FIG. 17 depicts plasmid construct pKS4-KB.

DETAILED DESCRIPTION OF THE INVENTION

Figure 1:
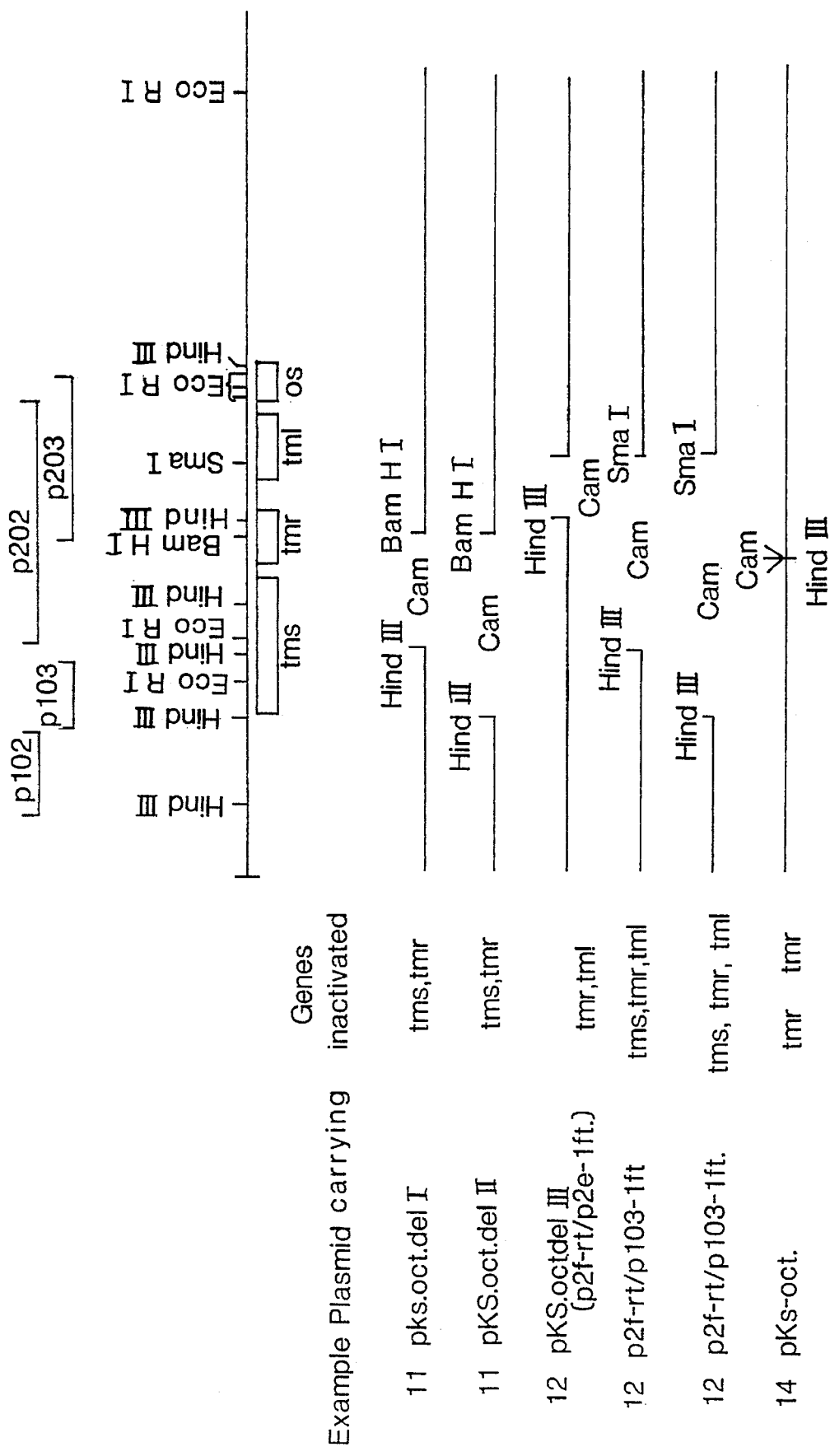
FIG. 1 depicts a comparison of plasmid constructs p102, p103, p202, p203, pKS-oct. delI, pKS-oct.delII, pKS-oct.delIII, p2f-rt/p103-1 ft, and pKS-oct.tmr.

The following definitions are provided, in order to remove ambiguity as to the intent or scope of their usage in the specifications and claims.

T-DNA: A segment of DNA derived from the transformation-inducing principle (TIP) which becomes integrated in the plant genome. As used herein, the term includes DNA originally derived from any tumor inducing strain of Agrobacterium including *A. tumefaciens* and *A. rhizogenes,* the latter sometimes referred to in the prior art as R-DNA. In addition, as used herein the term T-DNA includes any alterations, modifications, mutations, insertions and deletions, either naturally occurring or introduced by laboratory procedures, the only structural requirement being that sufficient of the right and left ends of naturally occurring T-DNAs be present to ensure the expected function of stable integration which is characteristic of al ) T-DNA.

plant gene: As used herein includes both structural and regulatory elements of a plant gene said elements being exogenous to the genes of T-DNA itself. As used herein, a plant gene is one in which both the promoter (a region of the gene which provides for and may regulate the initiation of transcription and the initiation of translation) and the structural gene (the region which codes for a protein and which may or may not contain one or more introns) are introduced into T-DNA from a plant source. The plant gene may also include a 3'-untranslated region which may function to regulate termination of transcription, and post-transcriptional RNA processing. The promoter and structural gene elements may be derived from the same, or different pre-existing genes and may be derived from the same or different plant sources. For example, a plant gene could be, as exemplified herein, a plant gene with its own promoter, or it could be an in vitro construct comprising the coding region (with or without introns) of one gene and the promoter of another, derived from the same or different plant species. The coding region of a plant gene, as herein defined, may include a cDNA copy of the structural portion of a plant gene. The promoter and coding regions may also include modifications, either naturally or artificially induced, and may include chemically synthesized segments. The coding segment may itself be a composite of segments derived from a plurality of sources, naturally occurring or synthetic, coding for a composite protein.

plant tissue: Includes differentiated and undifferentiated tissues of, and derived from higher plants including roots, shoots, pollen, seeds, tumor tissue, such as crown galls, and various forms of aggregations of plant cells in culture, such as embryos and calluses.

plant cell: As used herein includes plant cells in planta, and plant cells and protoplasts in culture.

Production of a genetically modified plant expressing a plant gene introduced via T-DNA combines the specific teachings of the present disclosure with a variety of techniques and expedients known in the art. In most instances, alternative expedients exist for each stage of the overall process. The choice of expedients depends on variables such as the choice of the basic TIP, the plant species to be modified and the desired regeneration strategy, all of which present alternative process steps which those of ordinary skill are able to select and use to achieve a desired result. The fundamental aspects of the invention are the nature and structure of the plant gene and its means of insertion into T-DNA. The remaining steps to obtaining a genetically modified plant include transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene from the originally transformed strain into commercially acceptable cultivars.

Figure 2:
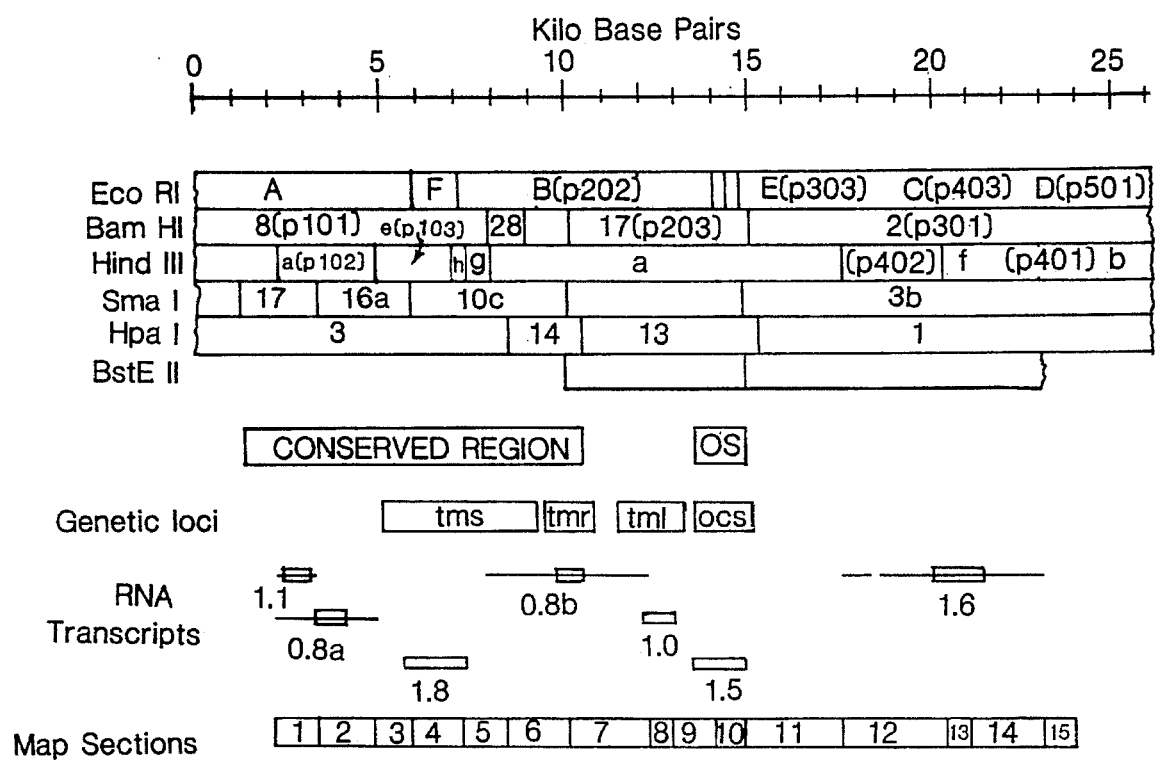
FIG. 2 depicts a map of the T-DNA region of pTi15955.

A principal feature of the present invention is the construction of T-DNA having an inserted plant gene, as defined supra. Location of the plant gene insertion site is not critical as long as the transfer function of sequences immediately surrounding the T-DNA borders are not disrupted, since these regions appear from prior art studies to be essential for insertion of the modified T-DNA into the plant genome. Preferred insertion sites are those which lie in areas that are most actively transcribed, in particular the tml gene and an area designated "1.6" lying in the HindIII-f fragment, and spanning map section 13, as shown in FIG. 2. No phenotype has been associated with the latter transcript. The term "1.6" is used herein to designate this actively transcribed region of T-DNA. T-DNA is obtained from any of the TIP plasmids. The plant gene is inserted by standard techniques well known to those skilled in the art. The orientation of the inserted plant gene, with respect to the direction of transcription and translation of endogenous T-DNA genes is not critical, either of the two possible orientations is functional. Differences in rates of expression may be observed when a given gene is inserted at different locations within T-DNA, possibly because of such factors as chromatin structure. Readily detectable levels of expression of the phaseolin gene have been obtained where that gene was inserted in a SmaI site within the tml gene of pTi15955, an octopine-type plasmid of *A. tumefaciens*.

A convenient means for inserting a plant gene into T-DNA involves the use of shuttle vectors, as described supra, having a segment of T-DNA (that segment into which insertion is desired) incorporated into a plasmid capable of replicating in *E. coli*. The T-DNA segment contains a restriction site, preferably one which is unique to the shuttle vector. The plant gene can be inserted at the unique site in the T-DNA segment and the shuttle vector is transferred into cells of the appropriate Agrobacterium strain, preferably one whose T-DNA is homologous with the T-DNA segment of the shuttle vector. The transformed Agrobacterium strain is grown under conditions which permit selection of a double homologous recombination event which results in replacement of a pre-existing segment of the Ti plasmid with a segment of T-DNA of the shuttle vector.

Following the strategy just described, the modified T-DNA can be transferred to plant cells by any technique known in the art. For example, this transfer is most conveniently accomplished either by direct infection of plants with the novel Agrobacterium strain containing a plant gene incorporated within its T-DNA, or by co-cultivation of the Agrobacterium strain with plant cells. The former technique, direct infection, results in due course in the appearance of a tumor mass or crown gall at the site of infection. Crown gall cells can be subsequently grown in culture and, under appropriate circumstances known to those of ordinary skill in the art, regenerated into whole plants that contain the inserted T-DNA segment. Using the method of co-cultivation, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker incorporated into the T-DNA in addition to the plant gene. Examples include either dihydrofolate reductase or neomycin phosphotransferase expresssed under control of a nopaline synthetase promoter. These markers are selected by growth in medium containing methotrexate or kanamycin, respectively, or their analogs. In addition, the T-DNA provides endogenous markers such as the gene or genes controlling hormone-independent growth of Ti-induced tumors in culture, the gene or genes controlling abnormal morphology of Ri-induced tumor roots, and genes that control resistance to toxic compounds such as amino acid analogs, such resistance being provided by an opine synthetase. Screening methods well known to those skilled in the art include assays for opine production, specific hybridization to characteristic RNA or T-DNA sequences, or immunological assays for specific proteins, including ELISA, (acronym for "enzyme linked immunosorbent assay") radioimmune assays and "western" blots.

An alternative to the shuttle vector strategy involves the use of plasmids comprising T-DNA or modified T-DNA, into which a plant gene is inserted, said plasmids being capable of independent replication in an Agrobacterium strain. Recent evidence indicates that the T-DNA of such plasmids can be transferred from an Agrobacterium strain to a plant cell provided the Agrobacterium strain contains certain trans-acting genes whose function is to promote the transfer of T-DNA to a plant cell. Plasmids that contain T-DNA and are able to replicate independently in an Agrobacterium strain are herein termed "sub-TIP" plasmids. A spectrum of variations is possible in which the sub-TIP plasmids differ in the amount of T-DNA they contain. One end of the spectrum retains all of the T-DNA from the TIP plasmid, and is sometimes termed a "mini-TIP" plasmid. At the other end of the spectrum, all but the minimum amount of DNA surrounding the T-DNA border is deleted, the remaining portions being the minimum necessary to be transferrable and integratable in the host cell. Such plasmids are termed "micro-TIP". Sub-TIP plasmids are advantageous in that they are small and relatively easy to manipulate directly. After the desired gene has been inserted, they can easily be introduced directly into a plant cell containing the trans-acting genes that promote T-DNA transfer. Introduction into an Agrobacterium strain is conveniently accomplished either by transformation of the Agrobacterium strain or by conjugal transfer from a donor bacterial cell, the techniques for which are well known to those of ordinary skill.

Regeneration is accomplished by resort to known techniques. An object of the regeneration step is to obtain a whole plant that grows and reproduces normally but which retains integrated T-DNA. The techniques of regeneration vary somewhat according to principles known in the art, depending upon the origin of the T-DNA, the nature of any modifications thereto and the species of the transformed plant. Plant cells transformed by an Ri-type T-DNA are readily regenerated, using techniques well known to those of ordinary skill, without undue experimentation. Plant cells transformed by Ti-type T-DNA can be regenerated, in some instances, by the proper manipulation of hormone levels in culture. Preferably, however, the Ti-transformed tissue is most easily regenerated if the T-DNA has been mutated in one or both of the Tmr and Tms genes. Inactivation of these genes returns the hormone balance in the transformed tissue towards normal and greatly expands the ease and manipulation of the tissue's hormone levels in culture, leading to a plant with a more normal hormone physiology that is readily regenerated. In some instances, tumor cells are able to regenerate shoots which carry integrated T-DNA and express T-DNA genes, such as nopaline synthetase, and which also express an inserted plant gene. The shoots can be maintained vegatatively by grafting to rooted plants and can develop fertile flowers. The shoots thus serve as parental plant material for normal progeny plants carrying T-DNA and expressing the plant gene inserted therein.

The genotype of the plant tissue transformed is often chosen for the ease with which its cells can be grown and regenerated in in vitro culture. Should a cultivar of agronomic interest be unsuitable for these manipulations, a more amenable variety is first transformed. After regeneration, the newly introduced foreign plant gene is readily transferred to the desired agronomic cultivar by techniques well known to those skilled in the arts of plant breeding and plant genetics. Sexual crosses of transformed plants with the agronomic cultivars yielded initial hybrid. These hybrids can then be back crossed with plants of the desired genetic background. Progeny are continuously screened and selected for the continued presence of integrated T-DNA or for the new phenotype resulting from expression of the inserted plant gene. In this manner, plants can be produced having a genotype essentially identical to the agronomically desired parents with the addition of the inserted plant gene, after a number of rounds of back crossing and selection.

EXAMPLES

The following Examples utilize many techniques well known and accessible to those skilled in the arts of molecular biology and manipulation of TIPs and Agrobacterium; such methods are not always described in detail. Enzymes are obtained from commercial sources and are used according to the vendor's recommendations or other variations known to the art. Reagents, buffers and culture conditions are also known to those in the art. Reference works containing such standard techniques include the following: R. Wu, ed. (1979) Meth. Enzymol. 68; J. H. Miller (1972) *Experiments in Molecular Genetics;* R. Davis et al. (1980) *Advanced Bacterial Genetics;* and R. F. Schleif and P. C. Wnesink (1982) *Practical Methods in Molecular Biology.*

With the exception of the plasmid IIc, plasmids, and only plasmids, are prefaced with a "p", e.g., p3.8 or pKS4. Cells containing plasmids are indicated by identifying the cell and parenthetically indicating the the plasmid, e.g., *A. tumefaciens.* (pTi15955) or K802 (pKS4-KB). Table 1 provides an index useful for identifying plasmids and their interrelationships. Table 2 provides an index of deposited strains. FIG. 1 provides a useful comparison of the constructions described in Examples 5, 6 and 8.

Example 1

The purpose of this example is to teach the expression of a non-T-DNA eukaryotic gene under control of its own promoter.

1.1 Preparation of special plasmid derivatives

A restriction site was removed from the plasmid pBR322 by digestion with HindIII filling in the single-stranded sticky-ends by DNA polymerase I, blunt-end ligation, transformation into K802, selection for tetracycline resistance, plasmid isolation from the drug resistant clones, and characterization with restriction enzymes to confirm elimination of the appropriate restriction site. The plasmid was labeled p350 (pBR322-HindIII).

Figure 3:
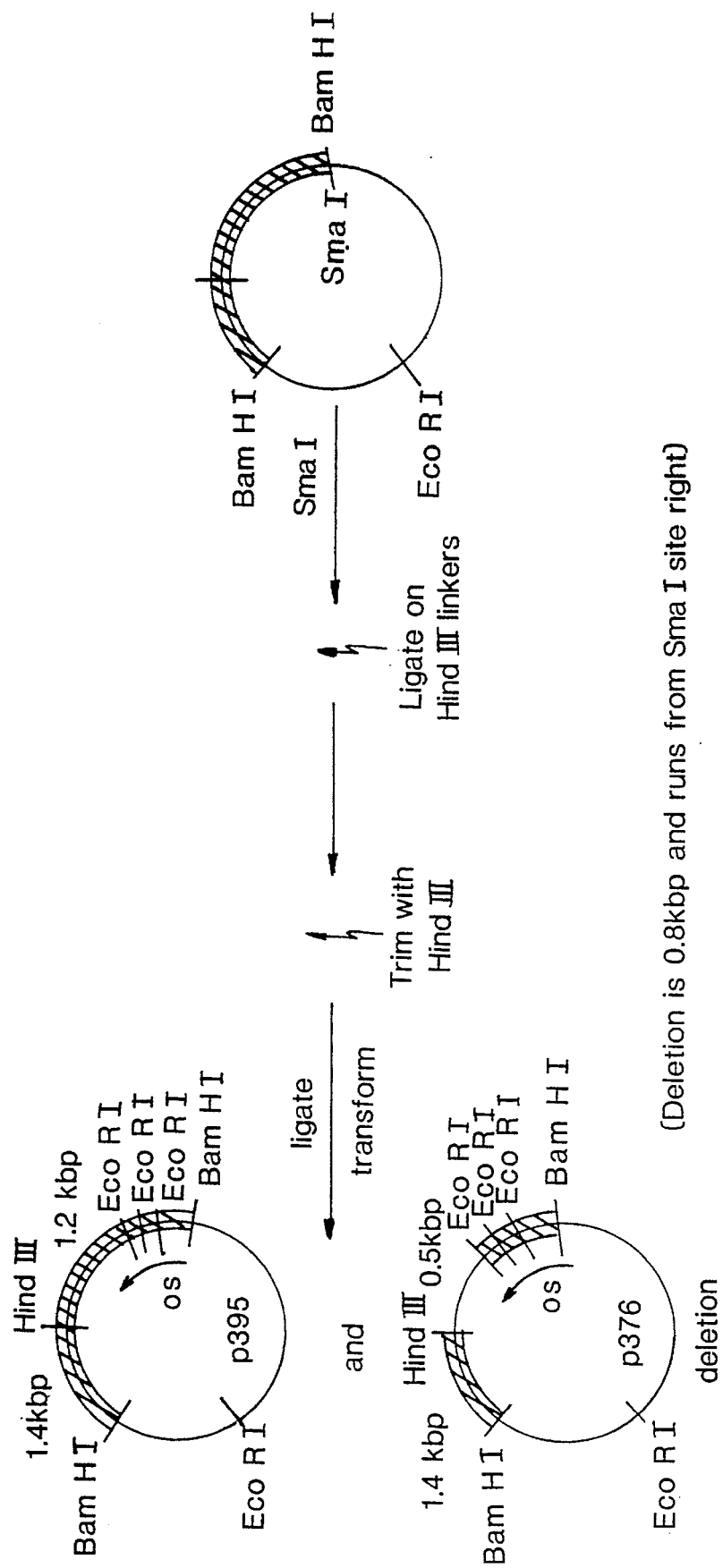
FIG. 3 depicts the derivation of plasmid p395 and p376.

1.2 Preparation of shuttle vectors p203 was digested with BamHI and the T-DNA Bam17 fragment (see FIG. 2) was isolated by agarose gel electrophoresis followed by elution from the gel. This fragment was mixed with and ligated to BamHI-linearized p350 and the reaction was transformed into K802. Plasmid isolated from ampicillin resistant transformants was characterized by restriction mapping, digested with SmaI, and blunt-end ligated to HindIII linkers. After the HindIII sticky-ends were unmasked by trimming with HindIII and the linearized plasmid was circularized by ligation to itself, the plasmid transformed into K802. Plasmid isolated from ampicillin resistant transformants was characterized by restriction mapping and a plasmid having a structure as shown in FIG. 3 was labeled p395. p376, to be discussed below, was also isolated at this point (FIG. 3).

p395 was digested with BamHI, and the Bam17 T-DNA fragment, which had had its SmaI site converted to a HindIII site, was isolated by agarose gel electrophoresis followed by elution. This Bam17 fragment was mixed with and ligated to BglII-linearized pRK290. The reaction mixture was transformed into K802, and after selection, transformants were used to prepare plasmids which were characterized by restriction mapping. The appropriate plasmid was labeled p490-8/14.

p376, whose derivation was described above in this example, was found to contain a deletion of about 0.8 kbp running to the right from the SmaI, now converted to the specificity of HindIII. As was done with p395 above, the BamHI T-DNA fragment corresponding to Bam17 was isolated and spliced into BglII-linearized pRK290. After transformation, selection, and plasmid isolation and characterization, the appropriate plasmid was labeled p458-1.

1.3 Insertion of the kanamycin resistance and phaseolin genes

Figure 4:
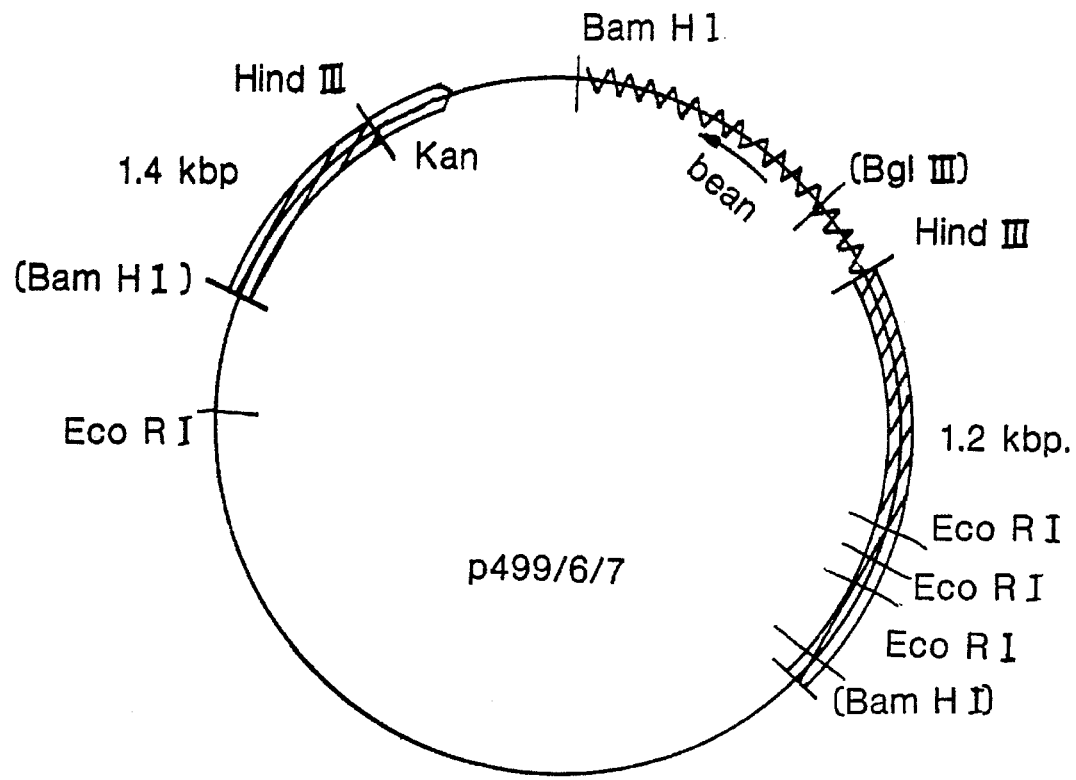
FIG. 4 depicts plasmid construct p499/6/7.
Figure 5:
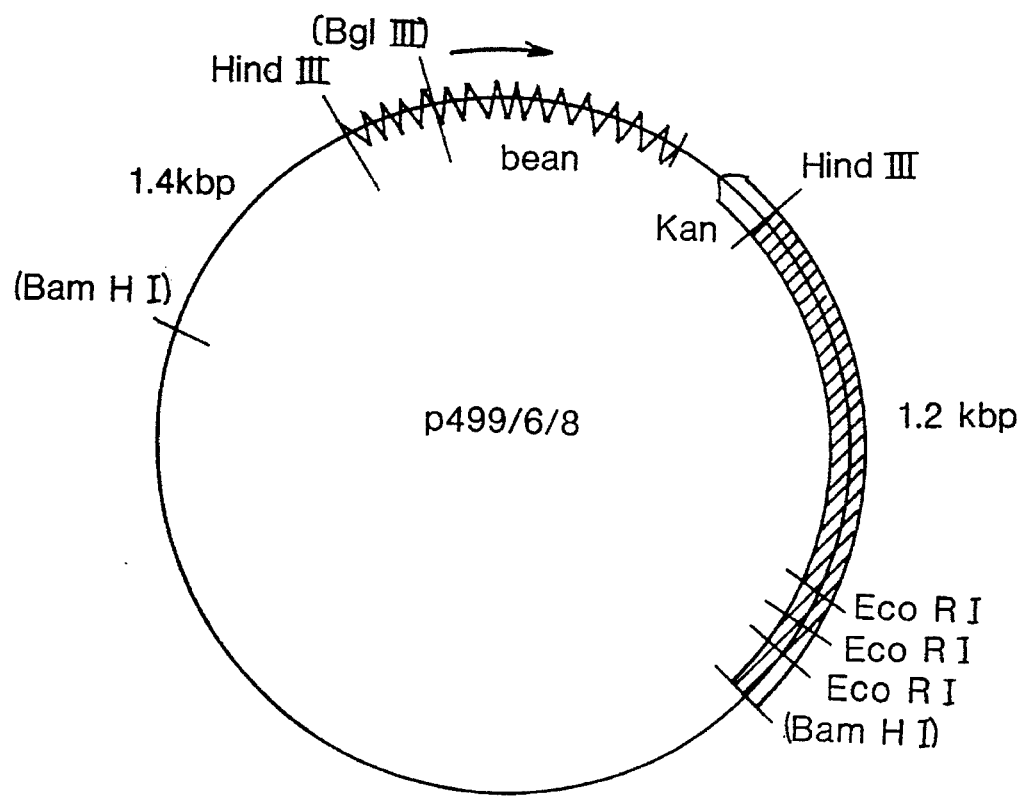
FIG. 5 depicts plasmid construct p499/6/8.

The phaseol in gene-carrying fragment was purified from HindIII digested pKS-KB3.8 by agarose gel electrophoresis. This fragment was mixed with and ligated to HindIII-linearized p490-8/14. Kanamycin resistant transformants of K802 were used to prepare plasmids which were then restriction mapped. Two constructions were isolated: p499/6/7 had bean sequences to the right of the kanamycin resistance (FIG. 4), and p499/6/8 had the opposite orientation (FIG. 5).

Figure 7:
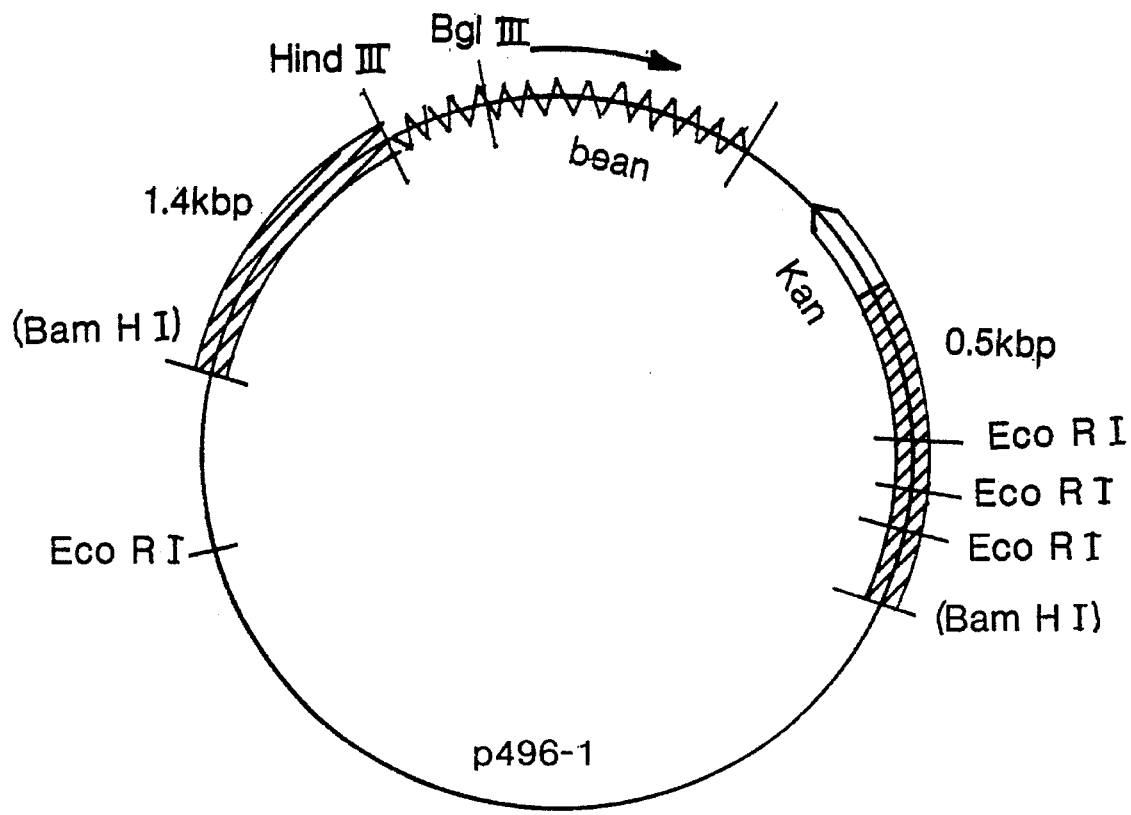
FIG. 7 depicts plasmid construct p496-1.
Figure 6:
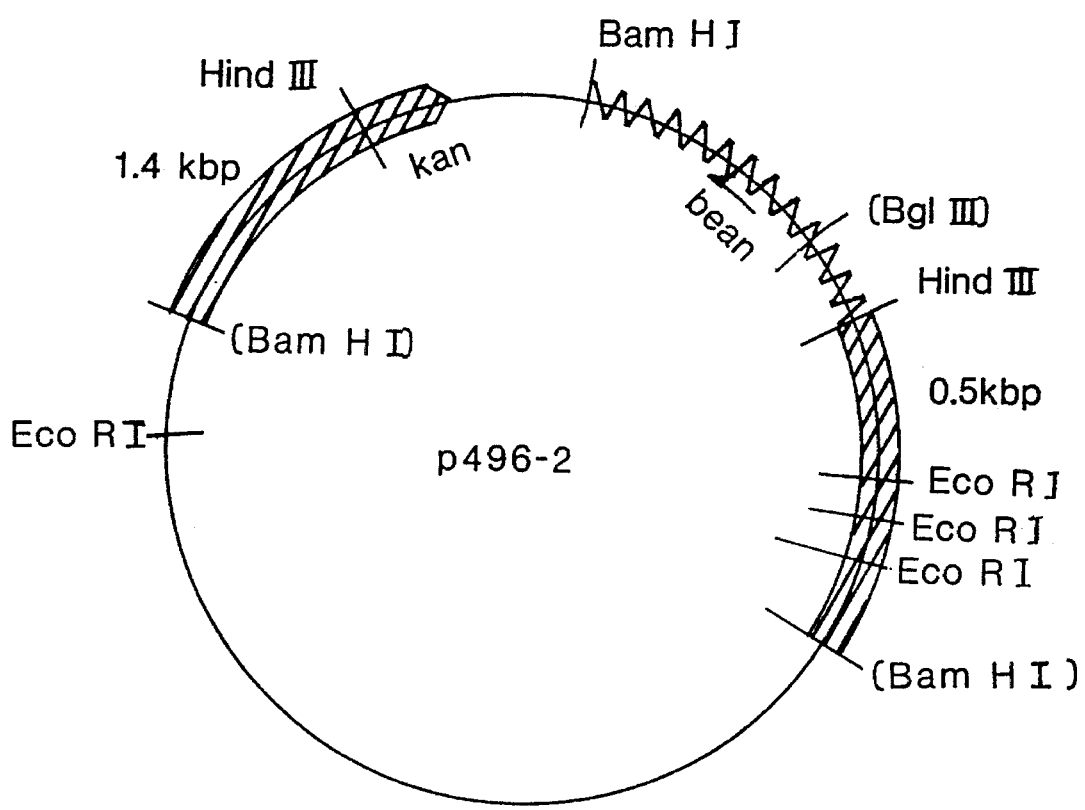
FIG. 6 depicts plasmid construct p496-2.

The purified HindIII fragment of pKS-KB3.8 carrying the phaseol in gene was also mixed with and ligated to HindIII-linearized p458-1. Plasmids were again prepared from kanamycin resistant transformants of K802 and restriction mapped. Again both orientations were isolated: p496-2 (FIG. 6.) and p496-1 (FIG. 7.) respectively had phaseolin to the right and left of the kanamycin resistance gene.

1.4 Double homologous recombination with Ti plasmids

The phaseolin and kanamycin genes were integrated into Ti plasmids harbored within Agrobacterium tumefaciens cells as described in Example 14. Two Ti plasmids were used as recipients: pTi15955, an octopine-type plasmid; and pTiA66, a strain derived from the A6 octopine-type plasmid which has a nonfunctional tms gene due to a natural insertion of an Agrobacterium IS (insertion) sequence. pTi15955 plasmids containing the constructions defined by p499/6/7, p499/6/8, p496-2, and p496-1, are respectively labeled p529-8, p529-7, p529-11 and p529-2. The same constructions in pTiA66 are respectively labeled p539-6, p539-5, p539-2, and p539-1.

1.5 Infection of plants

*A. tumefaciens* cells containing the Ti plasmids of the p529 and p539 series were used to infect stems of sunflower plants by puncture with a needle followed by injection of the appropriate bacterial cells.

1.6 Detection of phaseolin

Phaseolin protein sequences were detected to galls by ELISAs as described in Example 14. All galls tested were found to contain phaseolin; the level varied between 20 ng and 0 ng per gram tissue fresh weight, with the average being about 10 ng/g. Analysis by western blots of denaturing protein gels (SDS-polyacrylamide) showed discrete bands, of high apparent molecular weight, though significantly smaller than native phaseolin. The exact number and sizes of the bands varied between host plants, indicating that they were the results of host specific post-translational processing.

Phaseolin mRNA sequences were detected in galls as described in Example 12. All galls tested were found to contain phaseolin sequences in the poly(A)5+4RNA fraction; the level averaged about 0.005% of total poly(A)RNA. Analysis by northern blots of denaturing DNA gels (methyl mercury-agarose) showed a descrete band of high molecular weight the same size as natural phaseolin mRNA (1.6 kbp).

Phaseolin was also detected by ELISA in shoot tissue derived from cells infected with a pTiA66-based vector.

Detection levels of both phaseolin protein and phaseolin mRNA signals were significantly and substantially above the noise levels found when assaying galls transformed by *A. tumefaciens* cells harboring unmodified pTi15955 and unmodified pTiA66.

Example 2

This example teaches the insertion of complete phaseolin gene into T-DNA analogous to that taught in Example 1. This construction utilizes a shuttle vector designed to carry inserted sequences into a nopaline Ti plasmid, pTiC58, in the region of the nopaline synthetase gene.

2.1 Construction of a shuttle vector

Figure 10:
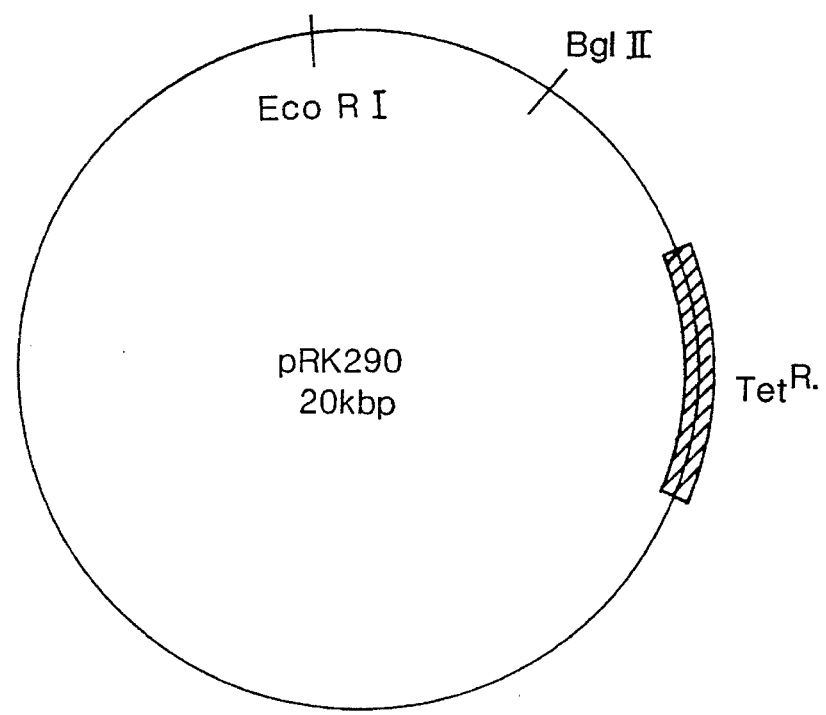
FIG. 10 depicts plasmid construct pRK290.

The nopaline-type plasmid, pTiC58 (FIG. 8a) was digested with SmaI, and a fragment encoding the nopaline synthetase gene was isolated by agarose gel electrophoresis. This fragment was blunt-end ligated to BglII linkers, which were then unmasked by digestion with BglII. The resulting DNA fragment was mixed with and ligated to BglII-linearized pRK290 (FIG. 10). Transformation into K802 was followed by selection with tetracycline, plasmid isolation, and restriction mapping. The appropriate plasmid was labeled pCF44A (FIG. 8b).

Figure 8:
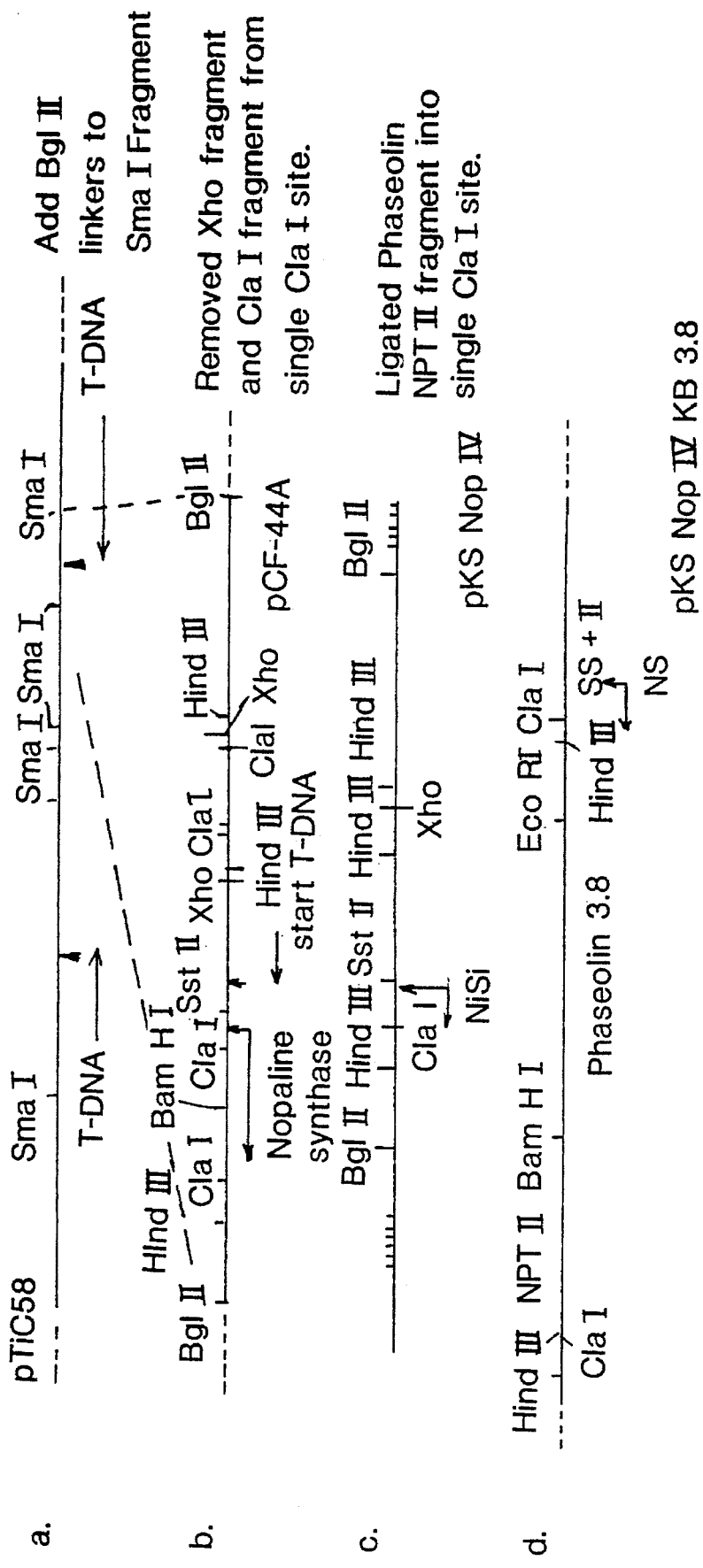
FIG. 8a is a linear depiction of plasmid pTiC58.
FIG. 8b is a linear depiction of plasmid pCF44A.
FIG. 8c is a linear depiction of plasmid pKS-nopIV.
FIG. 8d is a inear depiction of plasmid pKS-nopIV-KB3.8.
Figure 9:
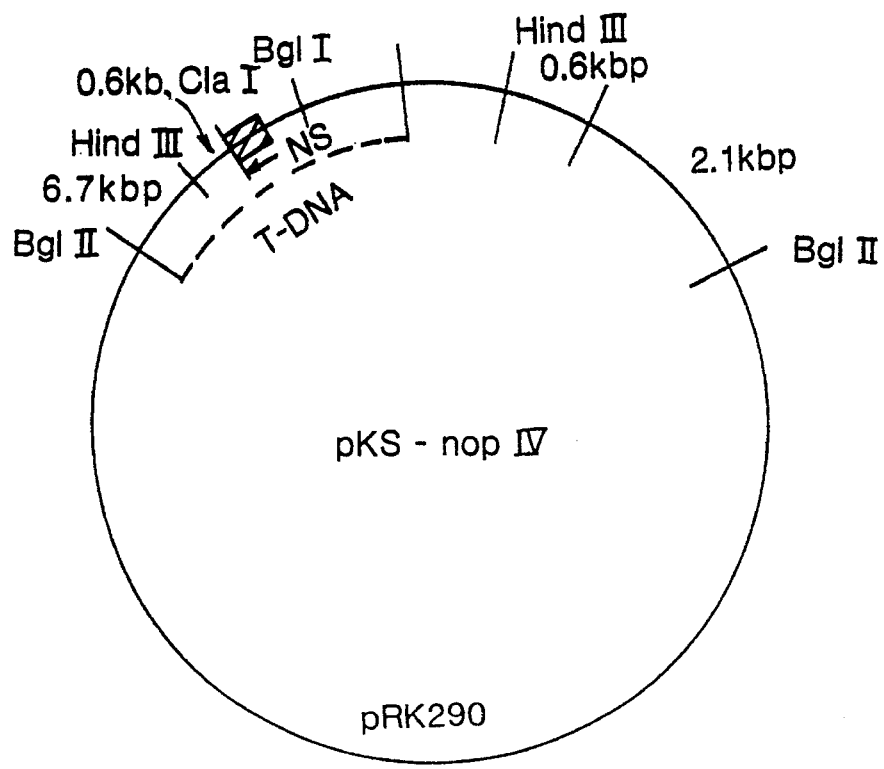
FIG. 9 depicts plasmid construct pKS-nopIV.

The four ClaI sites were reduced to a single ClaI susceptable site by serially resectioning pCF44A twice. The plasmid was digested with XhoI, religated to itself, and transformed into K802. After tetracycline selection, plasmid isolation, and restriction mapping, the appropriate plasmid having a deletion of an XhoI fragment which carries two ClaI sites was digested with ClaI, religated to itself, and transformed into K802. After selection, plasmid isolation, and restriction mapping the appropriate plasmid having a second deletion, this time of the ClaI fragment which carries all but the 5' end of the nos gene, was labeled pKS-nopIV (FIGS. 9, 8, 8c).

Figure 11:
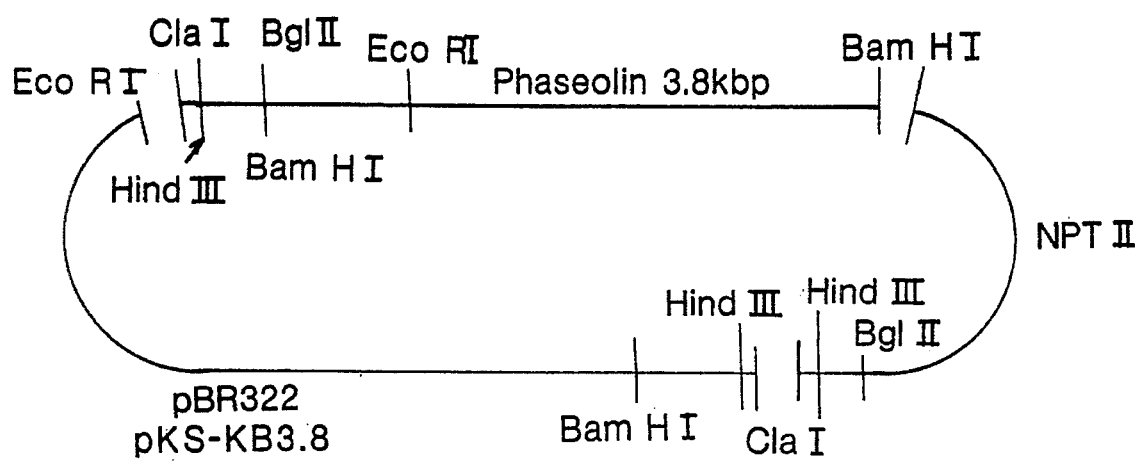
FIG. 11 depicts plasmid construct pKS-KB3.8.

2.2 Insertion of the kan/bean genes pKS-KB3.8 (FIG. 11) was digested with ClaI, and the 6.0 kbp fragment carrying the kanamycin resistance and phaseolin genes was isolated by agarose gel electrophoresis. This fragment was mixed with and ligated to ClaI-linearized pKS-nopIV, and transformed into K802. Plasmids isolated from transformants resistant to kanamycin and tetracycline and sensitive to ampicillin were restriction mapped and one having the structure shown in FIG. 8d was labeled pKS-nopIV-KB3.8A5. A similar clone oriented with the phaseolin gene to the left of the kanamycin resistance was found and labeled pKS-nopKB3.8Δ3.

12.3 Transfer to Ti plasmids and infection of plants

The triparental mating technique (see Background and Example 14) was used to transfer the constructions to pTiC58, a nopaline-type Ti plasmid. Ti plasmids C58-nopKBΔ3 and pC58-nop-KBΔ5, the results of matings of pKS-nopIVKB3.8Δ3 and Δ5, respectively, with pTiC58 were characterized by restriction site mapping and Southern blot analysis. Bacteria containing either of the two plasmids, having either orientation of the kanamycin resistance/phaseolin gene fragment nested within sequences from the 5' end of the nos gene and the nos gene's 3' flanking sequences, were used separately to infect stems of sunflower plants by puncture followed by injection of bacteria.

2.4 Detection of expression

Phaseolin gene expression was detected in sunflower gall tissue by ELISAs, as in Example 13.5.

Example 3

This example teaches manipulations of a gene for phaseolin, the major seed storage protein of the bean *Phaseolus vulgaris* L., preparatory to further manipulations which insert the phaseolin gene into vectors described in various other examples.

3.1 Subcloning of a phaseolin gene

Figure 12:
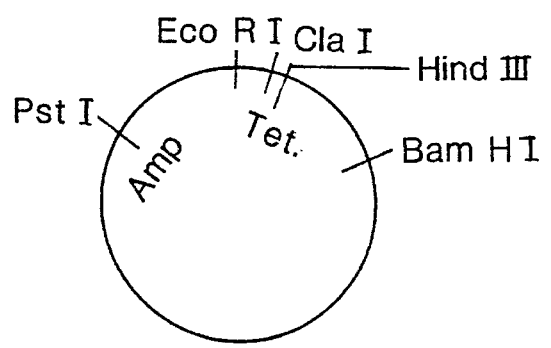
FIG. 12 depicts plasmid construct pBR322.
Figure 13:
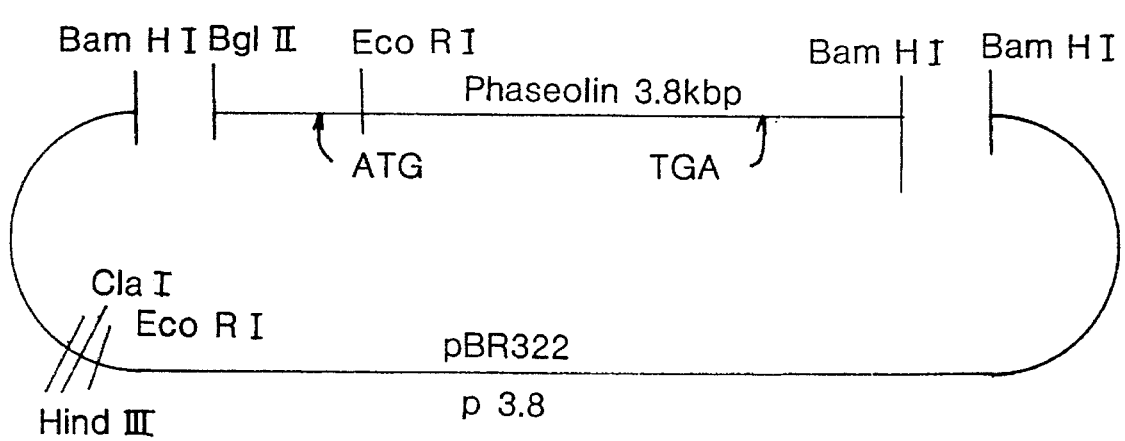
FIG. 13 depicts plasmid construct p3.8.
Figure 14:
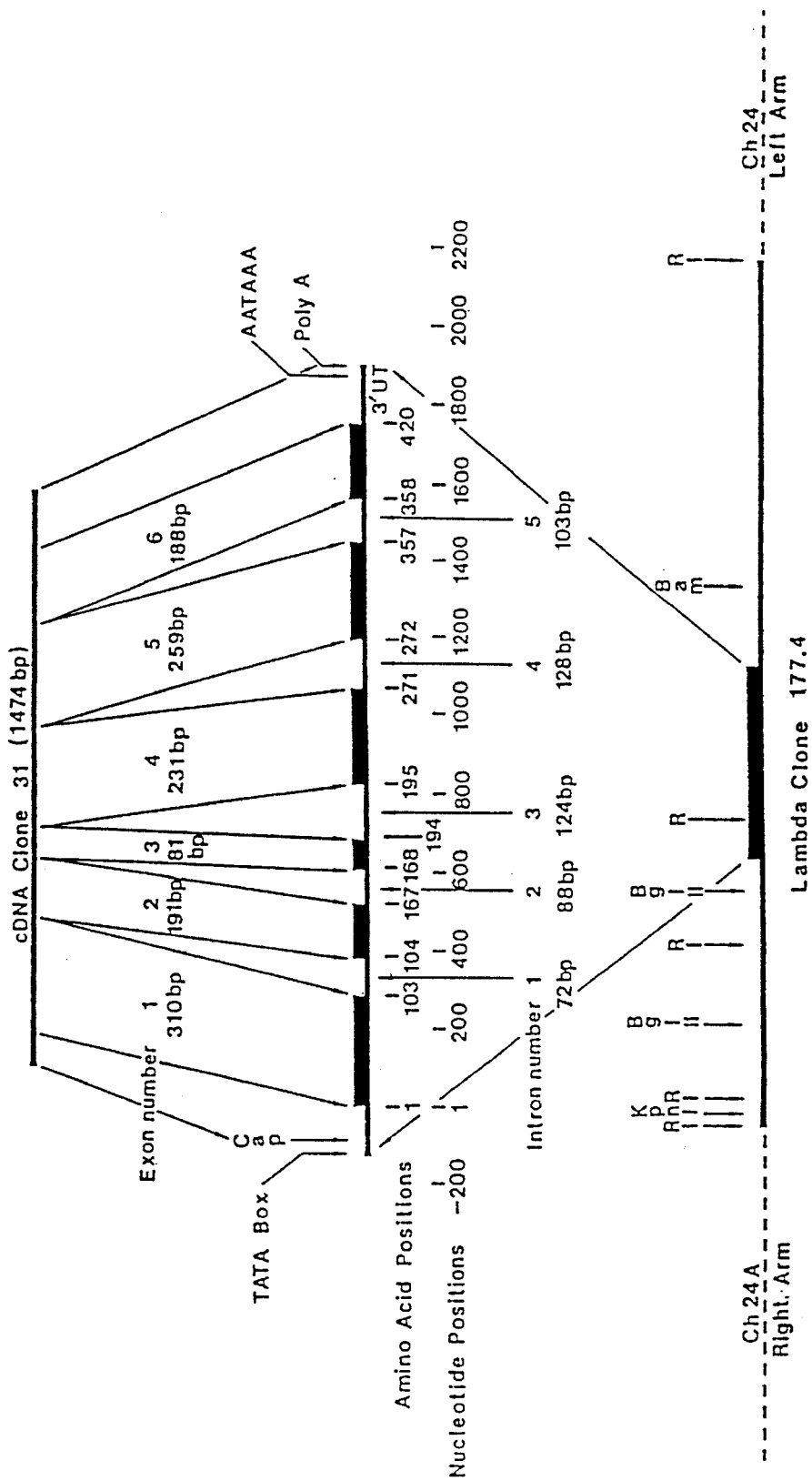
FIG. 14 depicts the structure of the phaseolin storage protein gene.

A genomic clone of phaseolin in a Charon 24A AG-PVPh177.4 (or 177.4; S. M. Sun et al. (1981) Nature 289:37–41, J. L. Slightore et al. (1983) Proc. Natl. Acad. Sci. USA 80; FIG. 14) was digested with BglII and BamHI. The 3.8 kbp fragment carrying the phaseolin gene and its flanking sequences, isolated by agarose gel electrophoresis, was mixed with and ligated to BamHI-linearized pBR322 (FIG. 12). The mixture was transformed into HB101, and colonies resistant to ampicillin and sensitive to tetracycline were selected. Plasmid isolated from these clones was restriction mapped. A plasmid having the structure shown in FIG. 13 was selected and labeled AGpPVPh3.8 (or alternatively, p3.8). The ligation of BB1II and BamHI sites with each other inactivates both sites.

Another subclone of 177.4 was constructed by digestion with EcoRI, isolation of a 7.2 kbp fragment containing extensive 3' flanking sequences and all but the extreme 5' end of the phaseolin gene, and isolated after ampicillin selection of HB101 transformants were restriction mapped. A plasmid having the insert oriented so that the HindIII site of pBR322 was adjacent to the 5' end of the phaseolin gene and distal to the 3' untranslated region was labeled AG-pPVPh7.2 (or p7.2; FIG. 15; Sun et al. and Slightom et al., supra).

3.2 Cloning and isolation of a kanamycin resistance gene pRZ102 (R. A. Jorgenson et al. (1979) Mol. gen. Genet. 177:65–72), a ColE1 plasmid carrying a copy of the transposon Tn5, was digested with BamHI and HindIII, mixed with pBR322 previously linearized with the same two enzymes, ligated, and transformed into K802. Plasmids, isolated from transformants selected for resistance to both ampicillin and kanamycin were restriction mapped and one having the structure shown in FIG. 16 was labeled pKS-4.

3.3 Linkage of the phaseol in gene with a kanamycin resistance p3.8 was digested with ClaI and BamHI, and a 4.2 kbp fragment containing the phaseolin gene and some pBR322 sequences was isolated by agarose gel electrophoresis. This was mixed with a ClaI/BamHI fragment of Tn5 carrying a kanamycin resistance (neomycin phosphotransferase II, NPTII) gene from pKS4 (FIG. 16) and pBR322 (FIG. 12) which had been linearized with ClaI. The mixture was ligated and transformed into K802. After selection of colonies resistant to ampicillin and kanamycin, plasmids were isolated and restriction mapped. A colony having the structure shown in FIG. 11 was labeled pKS-KB3.8.

p7.2 was digested with EcoRI and BamHI, and a 3.0 kbp fragment carrying all but the 5' end of the phaseolin gene was isolated by agarose gel electrophoresis. This was mixed with a HindIII/BamHI fragment of Tn5 carrying a kanamycin resistance gene from pKS4 (FIG. 16) and pBR322 (FIG. 12) which had been linearized with HindIII. The mixture was ligated and transformed into K802. After selection of colonies resistant to ampicillin and kanamycin, plasmids were isolated and restriction mapped. A colony having the structure shown in FIG. 17 was labeled pKS4-KB3. In pKS4-KB, phaseolin is missing sequences encoding the extreme 5' end of the gene, and all 5' flanking regions (see FIG. 14).

Example 4

This example teaches a method of removing the introns from a gene. This is the same as placing a cDNA in a genomic environment. Restriction enzyme sites are found, or created by site specific mutagenesis, in exons on both the 5' and 3' extremities of the unprocessed transcript. These sites exist in both the genomic clones and cDNA. The intervening intron-containing DNA can be removed from the genomic clone and be replaced with the corresponding intronless cDNA clone fragment spanning the two sites. The reverse operation is also possible: intron-containing genomic sequences can be placed in a cDNA environment. One inserts an internal fragment of the genomic clone into a corresponding gap cut out of a cDNA clone. This latter strategy is analogous, though often technically more difficult as the introns may contain sites susceptable to the enzymes chosen to create the exchanged fragment. This difficulty can be overcome by careful selection of conditions of partial digestion and by purification of the desired fragment by agarose gel electrophoresis. Further elaborations of this strategy include the manipulation of individual introns within a gene while leaving other introns and exons unaffected, and the stepwise exchange of sequences when inconvenient intervening restriction sites are present within introns as discussed above.

Figure 18:
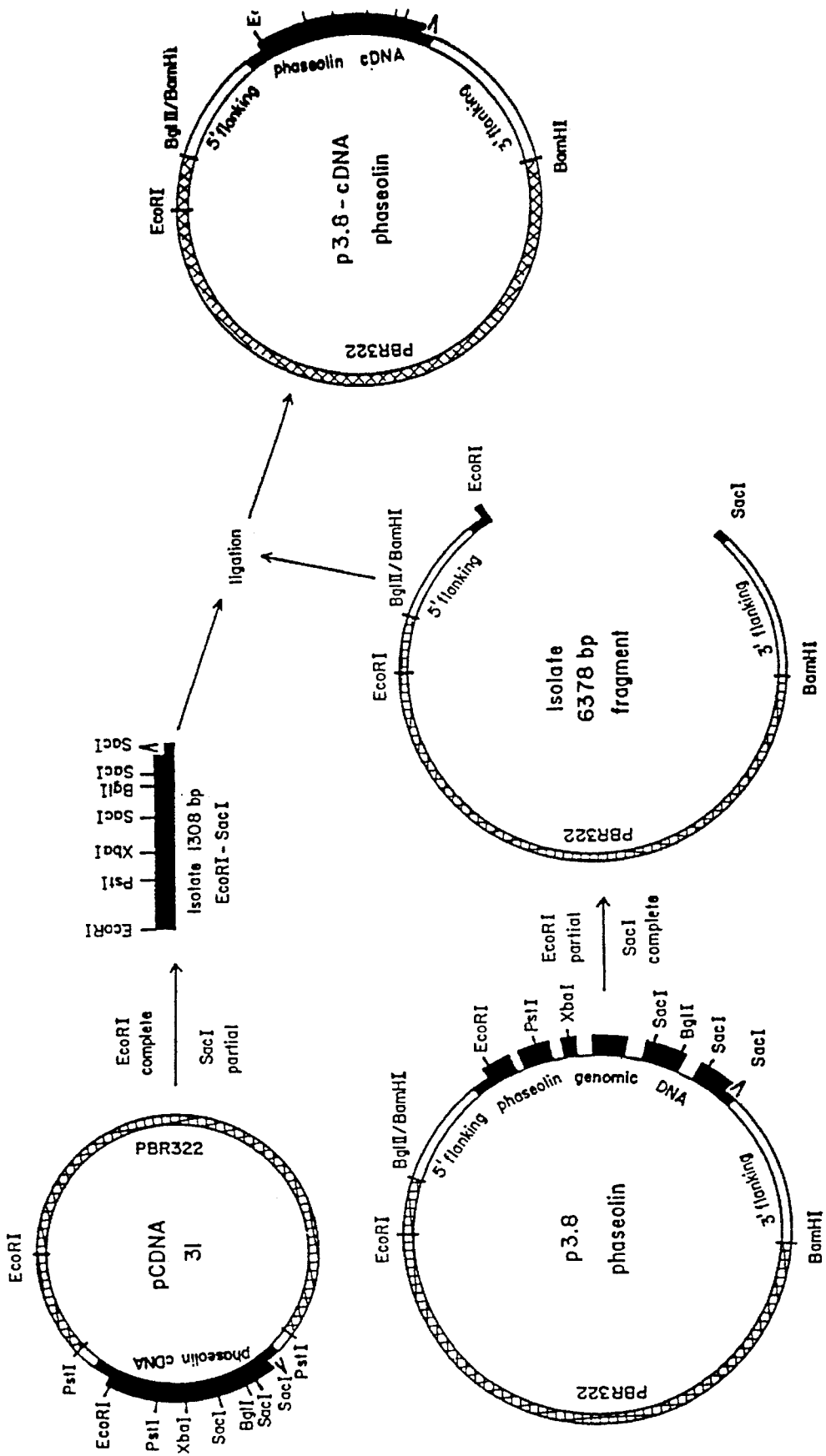
FIG. 18 depicts the construction of plasmid construct p3.8-cDNA.
Figure 22:
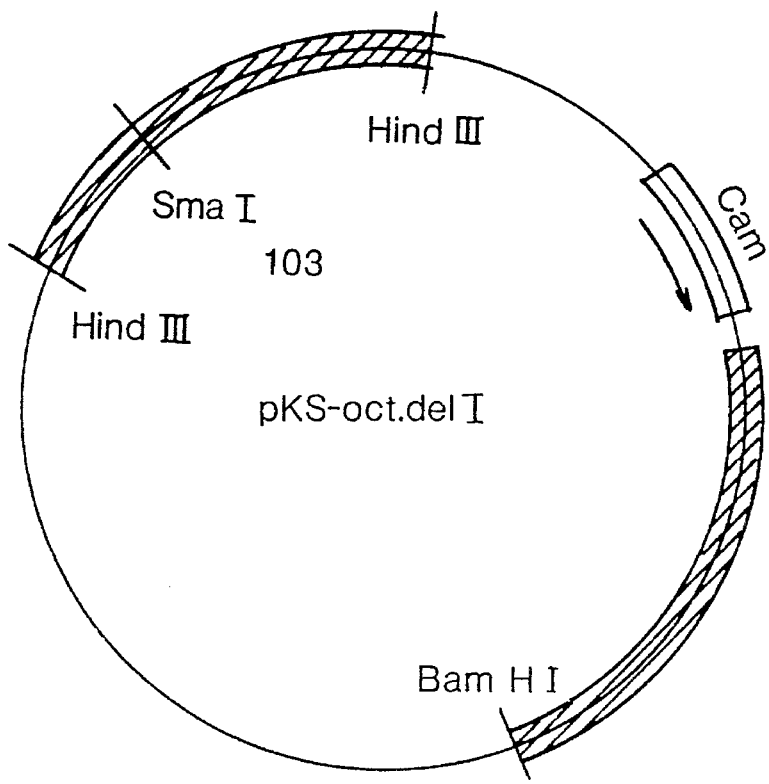
FIG. 22 depicts plasmid construct pKS-oct.delI.

4.1 Replacement of a fragment containing phaseolin's introns with cDNA p3.8, a plasmid clone of the phaseolin gene and its flanking sequences, was digested respectively partially and to completion with EcoRI and SacI, and a 6.4 kbp fragment, containing the pBR322 vector and both the 5' and 3' ends of the gene, was isolated by agarose gel electrophoresis. pcDNA31, a pBR322 plasmid clone of cDNA made from phaseolin mRNA, was digested respectively partially and to completion with SacI and EcoRI, and a 1.33 kbp fragment, containing the entire phaseolin cDNA except for sequences at the extreme 5' and 3' ends, was isolated by agarose gel electrophoresis. These two fragments were ligated together and transformed into HB101. After selection of colonies, growth of cells, and plasmid isolation, restriction mapping identified a plasmid having the desired structure. This plasmid was labeled p3.8-cDNA (FIG. 22). The entire construction is diagrammed in FIG. 18.

4.2 Use of p3.8-cDNA

Note that p3.8-cDNA can substitute for the genomic DNA source, e.g., p3.8, used in all other Examples, and that when so used will result in analogous constructions differing in that they are lacking introns. Alternatively, this strategy can be used to remove introns from constructions already made.

Example 5

The purpose of this example is to generate a Ti plasmid with a deletion from the tms ("shooting" locus) through the tmr ("rooting" locus) of pTi15955 and other octopine Ti plasmids. This derivative is useful because cells transformed by it are easier to regenerate to whole plants than cells transformed by pTi15955 with intact tms and tmr genes.

The tms-tmr deleted pTi15955 is ultimately changed in two ways: the in activation of tms-tmr and the insertion of a foreign gene. Should these two changes be located at different points of the T-DNA, each change is inserted independently by different shuttle vectors. Each shuttle vector dependent change is selected independently which will necessitate use of at least two markers selectable in Agrobacterium. In addition to the usual kanamycin resistance, this example utilized a chloramphenicol resistance derived from pBR325.

Figure 19:
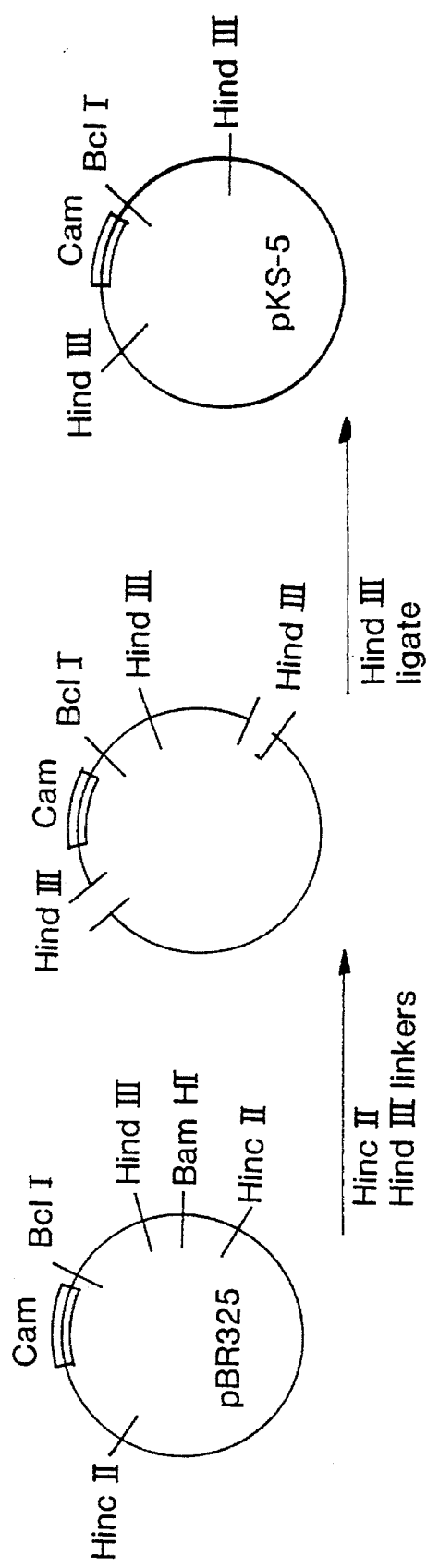
FIG. 19 depicts the construction of plasmid construct pKS-5.

5.1 Construction of a chloramphenicol resistance gene clone pBR325 is digested with HincII and blunt end ligated with HindIII linkers. The resultant preparation is digested with HindIII, religated, selected for chloramphenicol resistance (cam), and labeled pKS-5 which will serve as a source of the HindIII/BClI fragment which contains the cam gene (FIG. 19).

5.2 Construction of a pBR322 clone of T-DNA with a deletion and a cam gene

Figure 20:
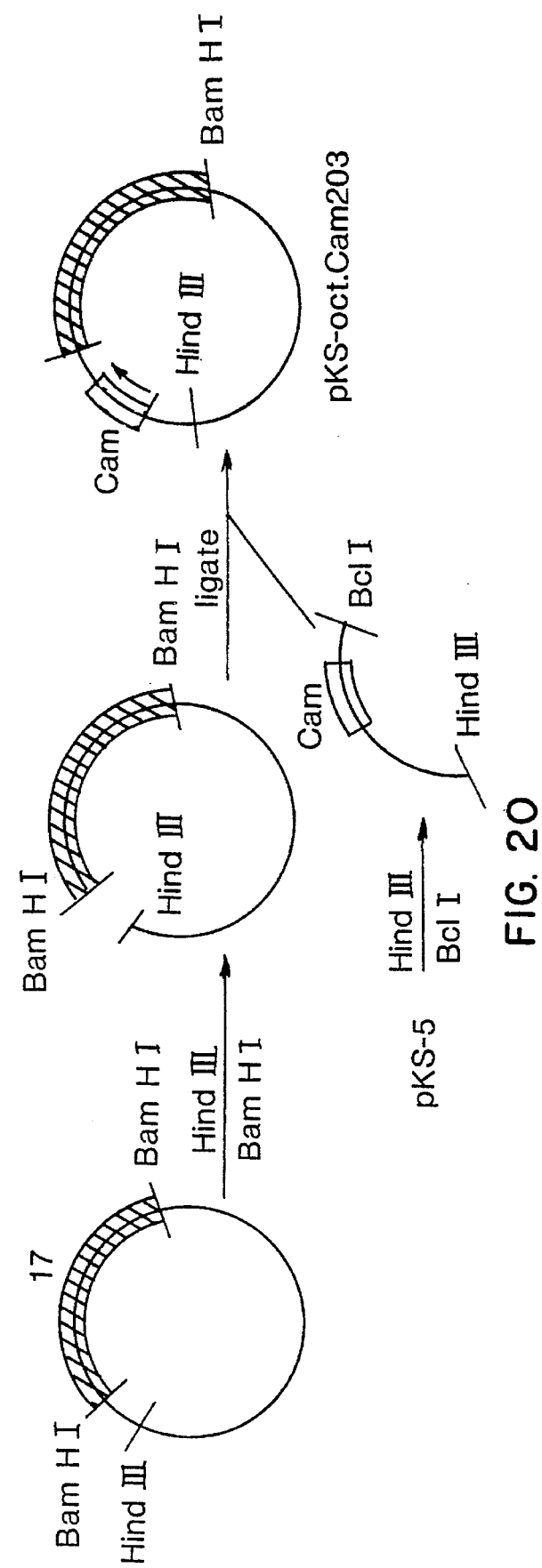
FIG. 20 depicts the construction of plasmid construct pKS-oct.Cam203.
Figure 21:
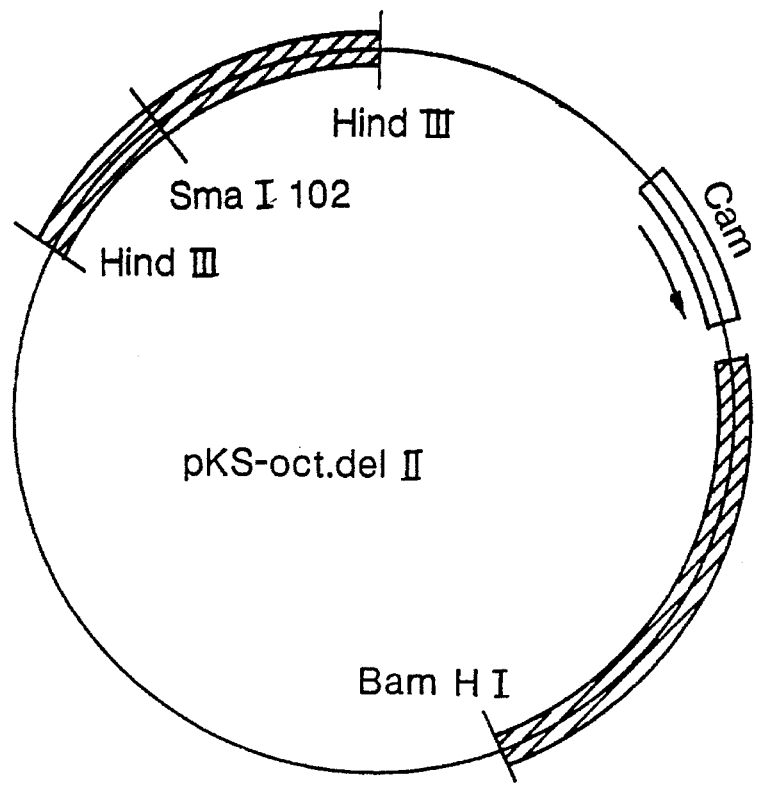
FIG. 21 depicts plasmid construct pKS-oct.delII.
Figure 31:
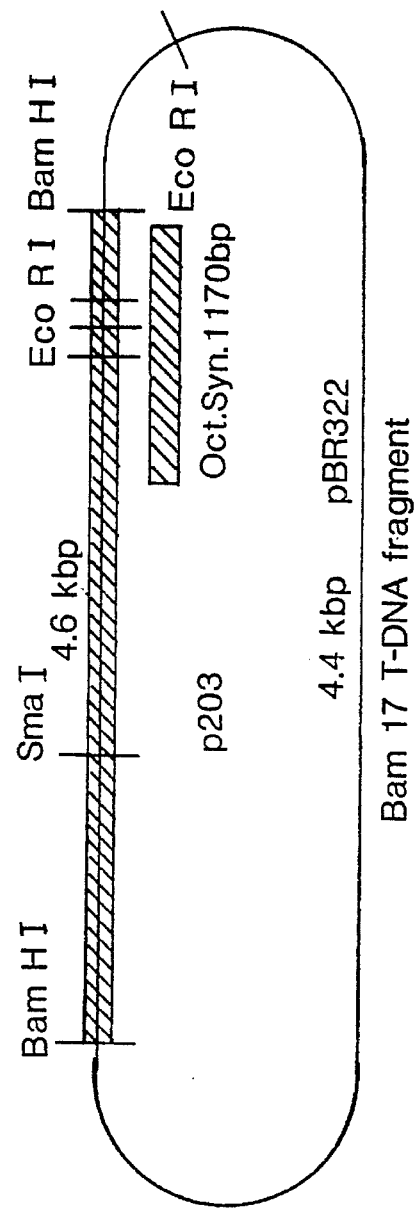
FIG. 31 depicts plasmid construct p203.
Figure 32:
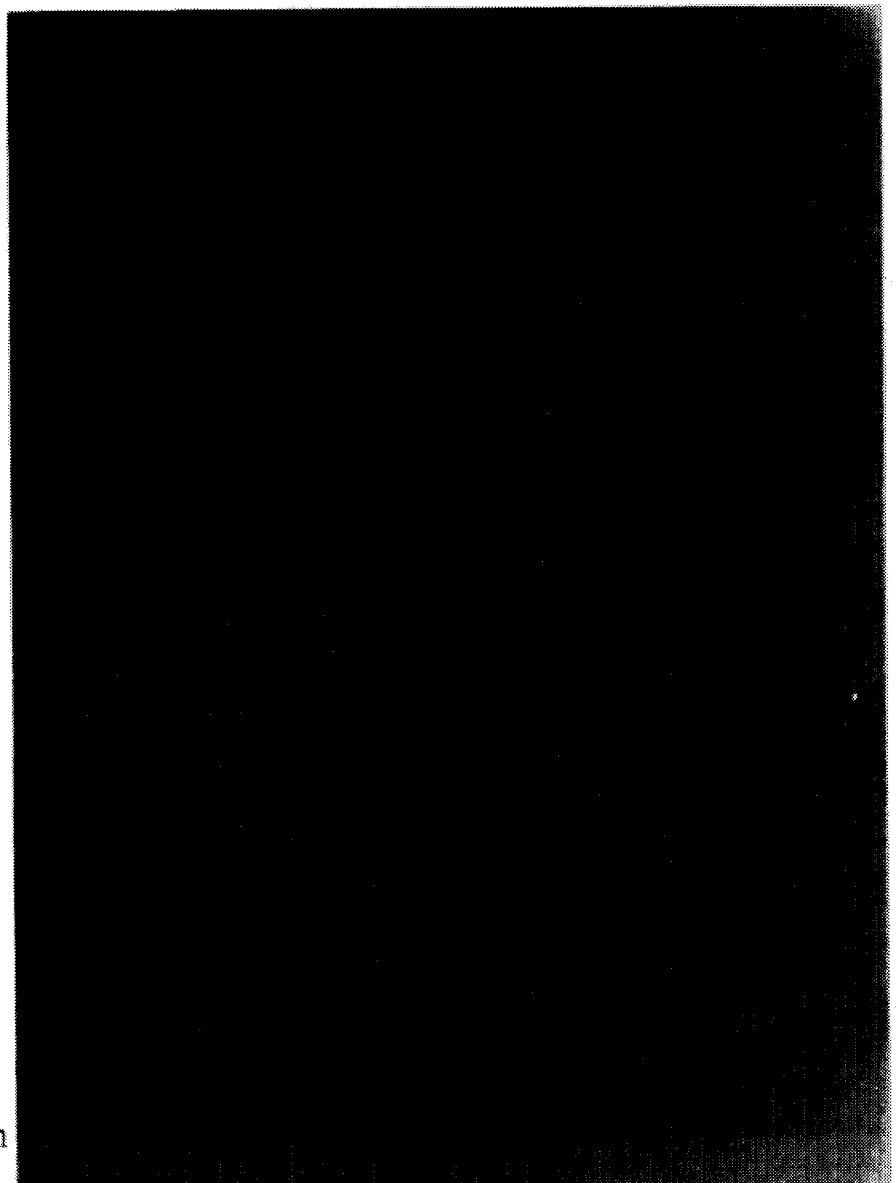
FIG. 32 is a photograph of a gel demonstrating the pressure of phaseolin in germinating transformed tobacco seeds.

A 9.2 kbp linear DNA fragment is isolated from a complete HindIII and partial BamHI digest of p203 (FIG. 31). The fragment carrying the cam gene is isolated from pKS-5, mixed with the 9.2 kbp linear fragment, ligated, transformed into *E. coli*, selected for chloramphenicol resistance, and labeled pKS-oct.Cam203 (FIG. 20).

pKS-oct.Cam203 is a plasmid clone that can now be used to construct a number of deletion TL mutants of pTi15955. It contains the right hand arm of TL and a resistance gene to the left of the right arm. Various left- hand arms of TL can be attached to the left of the cam gene (HindIII site). For instance, if p102 is attached the deletion is 5.2 kbp long and includes all of tms and tmr. If p103 is attached the deletion is 3.2kbp long and includes part of tms and all of tmr. See FIG. 2.

pKS-oct.Cam203 is digested with HindIII. p102 or p103 is digested with HindIII and the 2.2 kbp or 2.0 kbp T-DNA fragment is isolated and ligated with the linearized pKS-oct.Cam203, transformed, isolated yielding pKS-oct.delII (FIG. 21) or pKS-oct.delI (FIG. 22) respectively. These constructions are moved into *A. tumefaciens* by mating, homologous recombinations, and selection for chloramphenicol resistance. Alternatively, one moves the constructions into pRK290 by use of established methods by linearizing the construction carrying plasmids with BamHI and ligating into the BglII site of pRK290.

Example 6

The Ti plasmid is mutated in this example by deleting the T-DNA between the HpaI site in tmr to the SmaI site in tml. The Ti plasmids that can be modifed include pTi15955, pTiB6, pTiA66 and others. This construction is diagramed in FIG. 23.

6.1 Isolation of the cam gene pKS-5 (FIG. 19) is digested with HindIII and BclI. The smallest fragment is isolated after separation on an agarose gel, as taught in Example 5.

6.2 Construction of a pBR322 clone of T-DNA with a deletion

Figure 23:
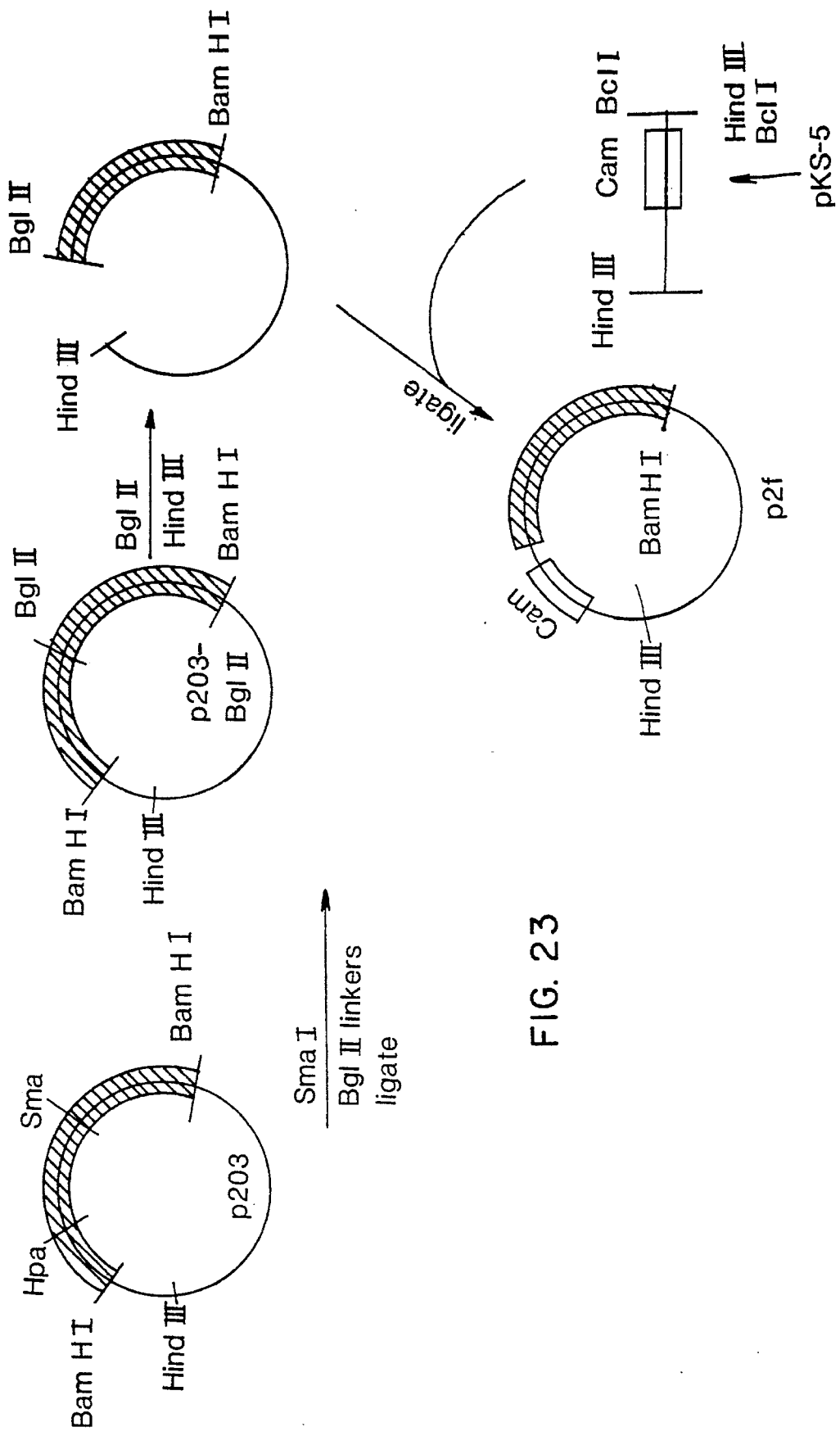
FIG. 23 depicts plasmid construction of plasmid construct p2f.

The right hand arm of the T-DNA deletion is constructed by insertion of a BglII site into the SmaI site of p203 (see FIG. 2). p203 is digested by SmaI, ligated with BglII linkers, digested with BglII, religated, and transformed into K802. In an alternative construction, BamHI linkers are substituted for BglII linkers and the appropriate BamHI partial digest products are isolated.) The resultant plasmid is labeled p203-BglII, and is digested with BglII and HindIII. The large BglII/HindIII vector containing fragment is ligated with the chloramphenicol resistance fragment whose isolation was described in Example 6.1. Chloramphenicol resistance is selected for after transformation into K802. The resultant plasmid is labeled p2f (FIG. 23).

6.3 Construction of left-hand arm of T-DNA deletion clone

Figure 24:
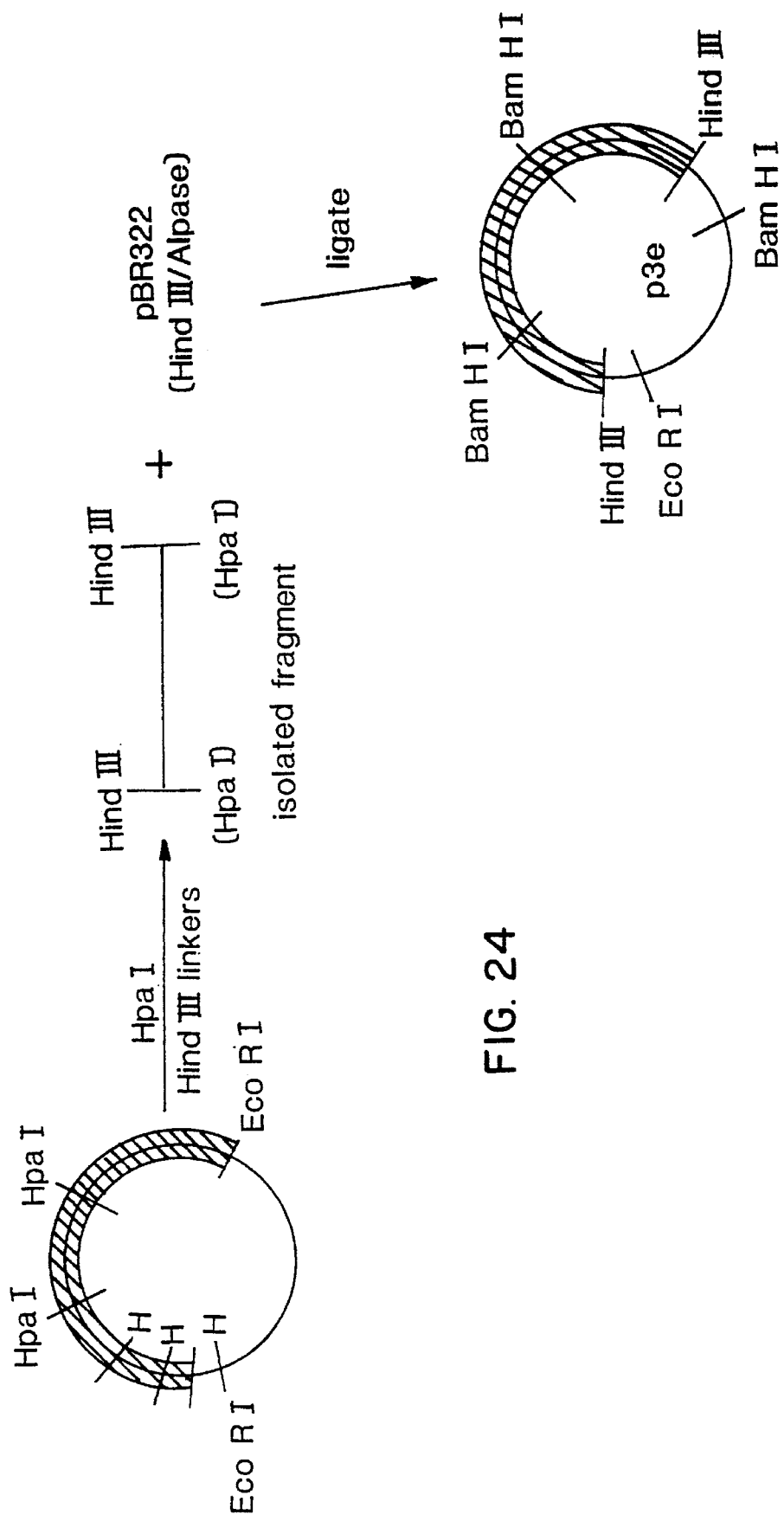
FIG. 24 depicts the construction of plasmid construct p3e.

HindIII sites are inserted into the HpaI site of p202 by digestion with HpaI and ligation with HindIII linkers. After unmasking of the HindIII sticky ends by digestion with that restriction enzyme, the 2 kbp HpaI fragment which now bears HindIII ends is isolated. HindIII digested HindIII-ended fragment and transformed into K802. After a colony containing the desired construction is isolated, and characterized, the plasmid is labeled p3e (FIG. 24).

6.4 Construction of the T-DNA deletion clone

Figure 25:
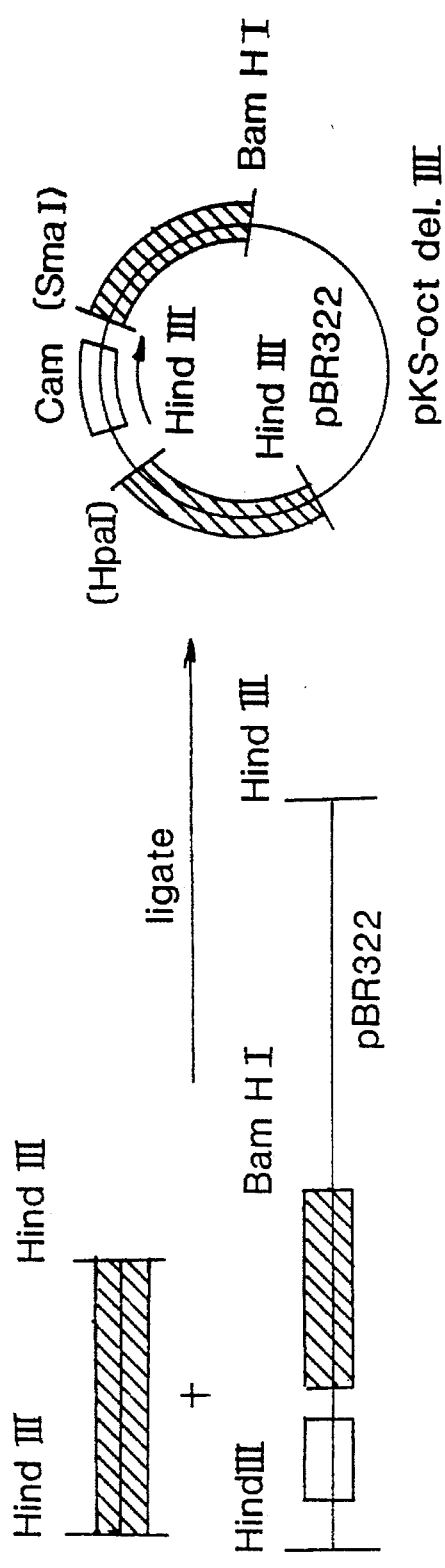
FIG. 25 depicts the construction of plasmid construct pKS-oct.delIII.

The left-hand arm of the clone is obtained by purifying a 2 kbp fragment of a HindIII digest of p3e by elution from an agarose gel after electrophoresis. p2f is cut by HindIII, treated with alkaline phosphatase, mixed with the 2 kbp fragment, ligated, transformed into K802, and selected for chloramphenicol resistance. Plasmids are isolated from individual colonies and characterized by restriction mapping. A plasmid having the two arms in the desired tandem orientation is chosen and labeled pKS-oct.delIII (FIG. 25).

pKS-Oct.delIII is moved into *A. tumefaciens* by mating, and homologous recombinants are selected by selection with chloramphenicol. Sunflower and tobacco roots and shoots are inoculated as described in other Examples and the tumors generated are tested for opines.

Example 7

This example teaches a construction deleting tmr and tml that provides an alternative to that taught in Example 6.

Figure 26:
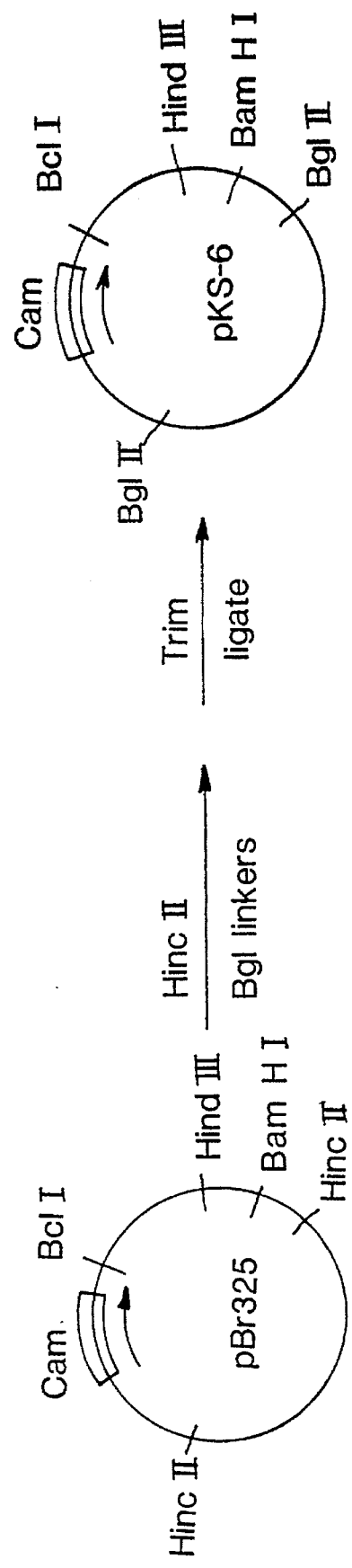
FIG. 26 depicts the construction of plasmid construct pKS-6.

7.1 Construction of a chloramphenicol resistant fragment with a BglII site pBR325 is digested with HincII, blunt-end ligated with BglII linkers, digested with BglII, and religated (FIG. 26). Chloramphenicol resistance is selected for after transformation of either K802 or GM33. The resultant plasmid, pKS-6 serves as a source of the Bglii/BclI fragment carrying the cam gene.

Figure 27:
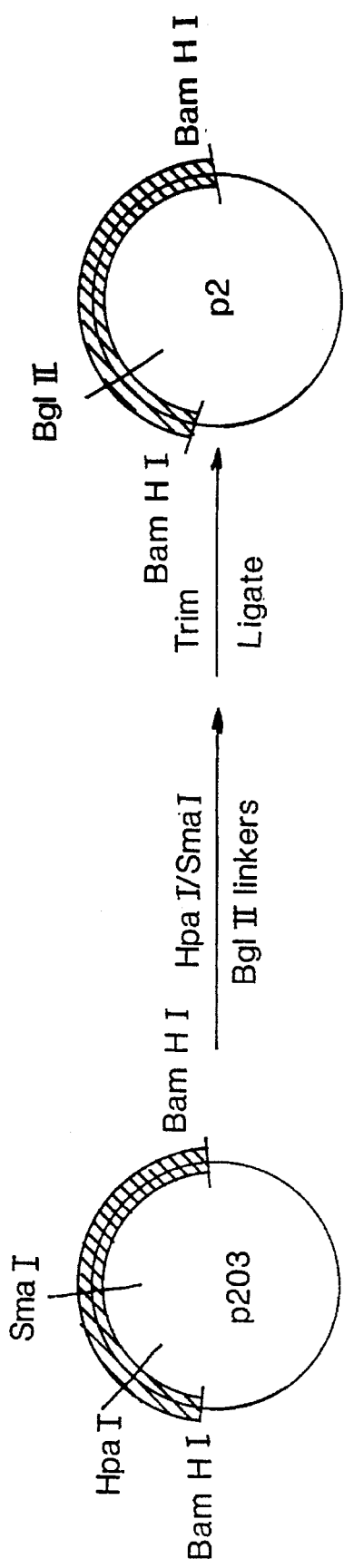
FIG. 27 depicts the construction of plasmid construct p2.

7.2 Construction of the tmr, tml deletion clone p203 is digested with HpaI and SmaI. After blunt end ligation with BglIII linkers, is it digested with BglII to expose the BglIII sticky ends, religated, and transformed into K802. The desired construction is identified and labeled p2 (FIG. 27).

7.3 Construction of the T-DNA deletion clone

Figure 28:
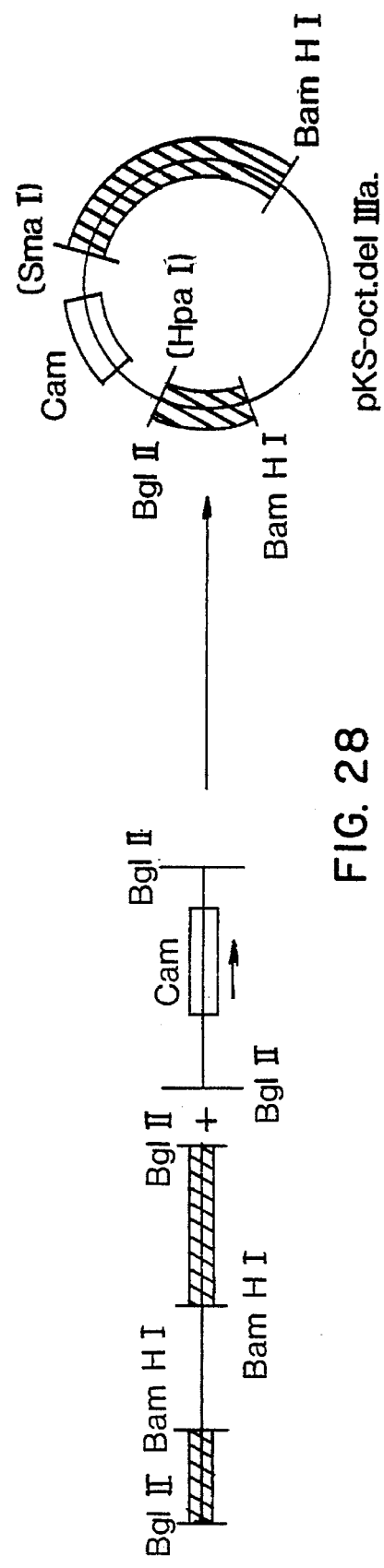
FIG. 28 depicts the construction of plasmid construct pKS-oct.delIIIa.

The BglIII fragment carrying the cam gene is isolated from pKS-6 and ligated into BglII-cut p2. Chloramphenicol resistance is selected for after transformation of K802. The resultant plasmid is labeled pKS-oct.delIIIa (FIG. 28), and is tested as described in Example 6.4.

Example 8

The purpose of this construction is to provide an example of the mutation of the tmr locus only at the Hpa site by insertion of the chloramphenicol resistance gene. This gene is isolated as the BglII/BclI fragment from pKS-6, and is ligated into the H.paI site of p203 after that site is changed to a BglII site.

Figure 29:
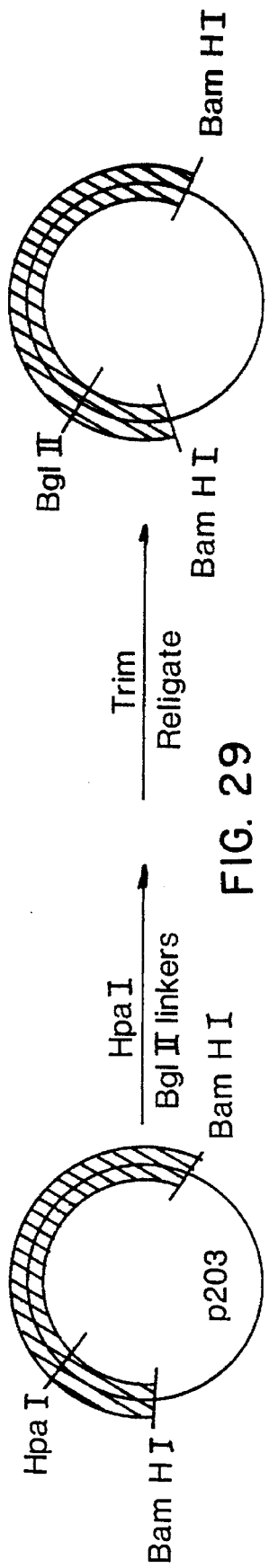
FIG. 29 depicts the insertion of BglII sites into plasmid p203.

8.1 Conversion of the Hpa site to a BglII site p203 is digested with Hpa, ligated to BglII linkers, trimmed with BglII and religated. After transformation of K802, colonies are selected and screened by restriction mapping for insertion of BglII sites (FIG. 29).

8.2 Isolation of the cam gene pKS-6 is digested with BglII and BclI. The smallest fragment is isolated by agarose gel electrophoresis.

8.3 Construction of the mutated T-DNA clone

Figure 30:
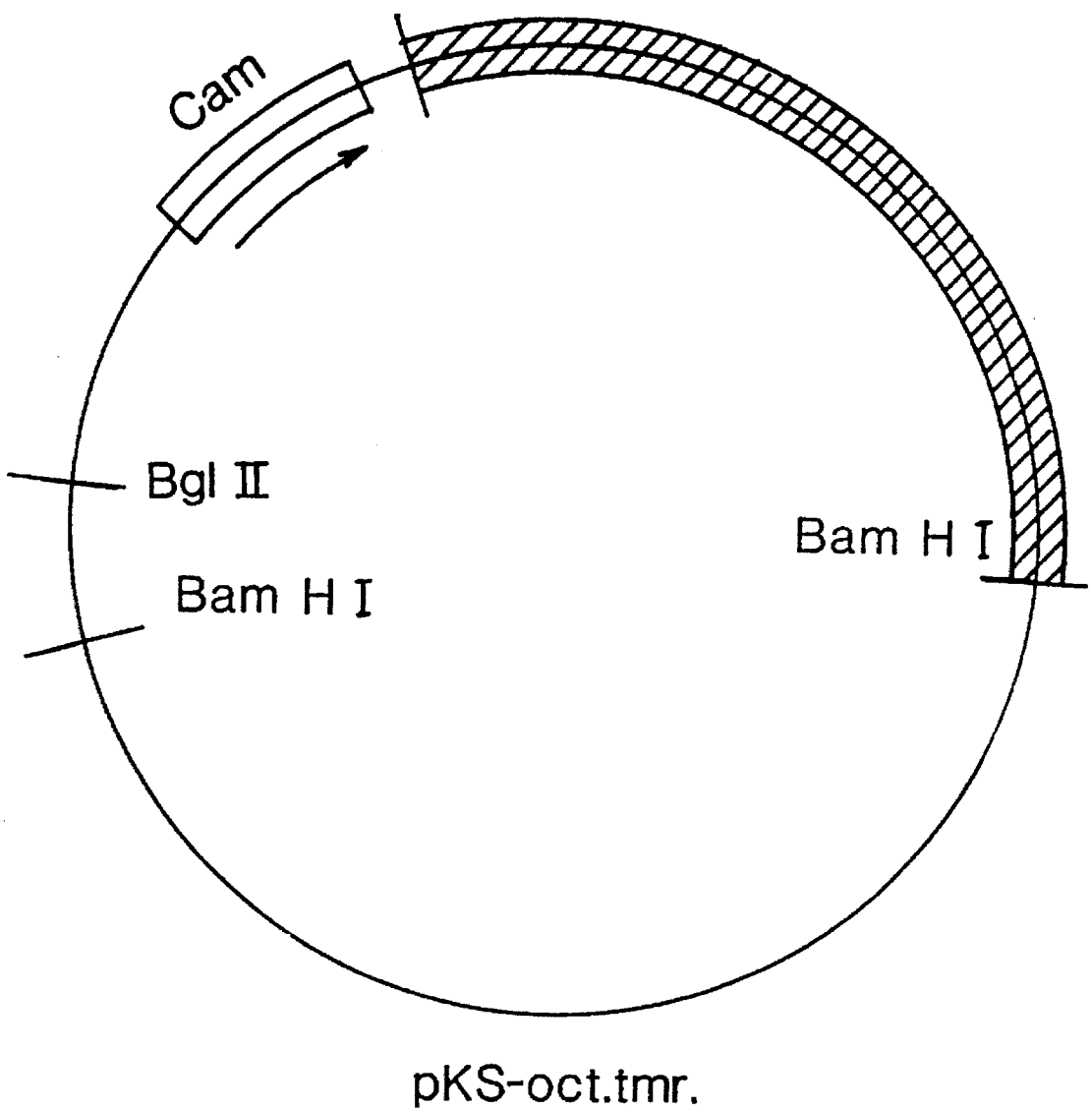
FIG. 30 depicts plasmid construct pKS-oct.tmr.

The modified p203 from Example 8.1 is digested with BglII, ligated with the purified cam gene from Example 8.2, and transformed into K802. Chloramphenicol resistance is selected for, and after isolation from the resistant transformants and characterization by restriction enzyme mapping, the plasmid is labeled pKS-oct.tmr (FIG. 30).

Example 9

Regeneration in this example involves carrot tumors incited by an Ribased TIP plasmid and is effected essentially as described by M.-D. Chilton et al. (1982) Nature 295:432–434.

9.1 Infection with hairy root

Carrot disks are inoculated with about $10^9$ bacteria in 0.1 ml of water. One to 1.5 cm segments of the ends of the roots obtained are cut off, placed on solid (1–1.5% agar) Monier medium lacking hormones (D. A. Tepfer and J. C. Tempe (1981) C. R. Hebd. Seanc. Acad. Sci., Paris 295:153–156), and grown at 25° C. to 27° C. in the dark. Cultures uncontaminated by bacteria are transferred every 2 to 3 weeks and are subcultured in Monier medium lacking hormones and agar.

9.2 Regeneration Of roots to plants

The cultured root tissue described in Example 9.1 is placed on solidified (0.8% agar) Monier medium supplemented with 0.36 μM 2,4-D and 0.72 μM kinetin. After 4 weeks, the resulting callus tissue is placed in liquid Monier medium lacking hormones. During incubation at 22° to 25° C. on a shaker (150 rpm) for one month, the callus disassociates into a suspension culture from which embryos differentiate, which, when placed in Petri dishes containing Monier medium lacking hormone, develop into plantlets. These plantlets are grown in culture, and after "hardening" by exposure to atmospheres of progressively decreasing humidity, are transferred to soil in either a greenhouse or field plot.

9.3 Use of non-hairy root vectors

Ti-based vectors which do not have functional tmr genes are used instead of the Ri-based vectors as described in Examples 9.1 and 9.2. Construction of suitable deletions is described in Example 6, 7, and 8.

Example 10

Regeneration in this example involves tobacco tumors incited by a Ti-based TIP plasmid and is effected essentially as described by K. A. Barton et al. (1983) Cell 32:1033–1043.

10.1 Infection with crown gall

Tobacco tissue is transformed using an approach utilizing inverted stem segments first described by A. C. Braun (1956) Canc. Res. 16:53–56. Stems are surface sterilized with a solution that was 7% commercial Chlorox and 80% ethanol, rinsed with sterile distilled water, cut into 1 cm segments, placed basal end up in Petri dishes containing agar-solidified MS medium (T. Murashige and F. Skoog (1962) Physiol. Plant. 15:473–497) lacking hormones. Inoculation is effected by puncturing the cut basal surface of the stem with a syringe needle and injecting bacteria. Stems are cultured at 25° C. with 16 hours of light per day. The calli which develop are removed from the upper surface of the stem segments, are placed on solidified MS medium containing 0.2 mg/ml carbenicillin and lacking hormones, are transferred to fresh MS-carbenicillin medium three times at interval s of about a month, and are tested to ascertain whether the cultures had been ridden of bacteria. The axenic tissues are maintained on solidified MS media lacking supplements under the culture conditions (25° C.; 16 hr.:8 hr. light:dark) described above.

10.2 Culture of transformed tissue

Clones are obtained from the transformed axenic tissues as described by A. Binns and F. Meins (1979) Planta 145:365–369. Calli are converted into suspensions of cells by culturing in liquid MS having 0.02 mg/l naphtalene acetic acid (NAA) at 25° C. for 2 or 3 days while being shaken at 135 rpm, and filtering in turn through 543 and 213 µum stainless steel meshes. The passed filtrate is concentrated, plated in 5 ml of MS medium containing 0.5% melted agar, 2.0 mg/l NAA, 0.3 mg/l kinetin and 0.4 g/l Difco yeast extract at a density of about $8 \times 10^3$ cells/mi. Colonies reaching a diameter of about 1 mm are picked by scalpel point, placed onto and grown on solidified MS medium having 2.0 mg/l NAA and 0.3 mg/l kinetin. The resulting calli are split into pieces and tested for transformed phenotypes.

10.3 Regeneration of plants

Transformed clones are placed onto solidified MS medium having 0.3 mg/l kinetin, and cultured as described in Example 10.1. The shoots which form are rooted by putting them on a solid (1.0% agar) medium containing 1/10 strength MS medium salts, 0.4 mg/l thiamine, lacking sucrose and hormones, and having a pH of 7.0. Rooted plantlets are grown in culture, hardened as described in Example 9.2, and are transferred to soil in either a greenhouse or field plot.

10.4 Vectors used

The methods described in Examples 10.1, 10.2 and 10.3 are suitable Ti-based vectors lacking functional tmr genes. Construction of suitable deletions is described in Examples 6, 7, and 8. These methods are also effective when used with Ri-based vectors. The method described in Example 10.1 for infection of inverted stem segments is often useful for the establishment of TIP transformed plant cell lines.

Example 11

Phaseolin is the most abundant storage protein (approximately 50% of the total seed protein) of *Phaseolis vulgaris*. Transfer of the functional phaseolin gene to alfalfa plants and translation of the phaseolin m-RNA into stored phaseolin is of significant economic value since it introduces storage protein synthesis into leaf material to be used as fodder. Alfalfa is a valuable plant for the transfer and expression of the phaseolin gene because of its acceptance as cattle fodder, its rapid growth, its ability to fix nitrogen through Rhizobial symbiosis, its susceptibility to crown gall infection and the ability to regenerate alfalfa plants from single cells or protoplasts. This example teaches the introduction of an expressible phaseol in gene into intact alfalfa plants.

11.1 Construction of shuttle vector

Alfalfa plants are regenerated from crown gall tissue containing genetically engineered Agrobacterium plasmids as described hereafter. In the first step we construct a "shuttle vector" containing a $tmr^-$ and a $tms^-$ T-DNA mutant linked to a functional phaseolin gene. This construction is, in turn, linked to a nopaline synthetase promoter which has a functional neomycin phosphotransferase (NPTII) structural gene (kanamycin resistance) downstream (reported by M.-D. Chilton, et al. (18 Jan. 1983) 15th Miami Winter Symposium; see also J. L. Marx (1983) Science 219:830 and R. Horsch et al. (18 Jan. 1983) 15th Miami Winter Symposium). This type of construction is illustrated in Example 1.

11.2 Transfer to Agrobacterium and plant cells

The "shuttle vector" is then transformed by conventional techniques (Example 14) into a strain of Agrobacterium containing a Ti plasmid such as pti15955. Bacteria containing recombinant plasmids are selected and cocultivated with alfalfa protoplasts which are regenerated cell walls (Marton et al. (1979) Nature 277:129–131; G. J. Wullems et al. (1981) Proc. Nat. Acad. Sci. USA 78:4344–4348; and R. B. Horsch and R. T. Fraley (18 Jan. 1983) 15 Miami Winter Symposium).

Cells are grown in culture and the resulting callus tissue is tested for the presence of the appropriate mRNA by Northern blotting (Example 12) and for the presence of the appropriate proteins by ELISA tests (see J. L. Marx (1983) Science 219:830; R. B. Horsch and R. T. Fraley (18 Jan. 1983) 15th Miami Winter Symposium).

11.3 Plant regeneration

Alfalfa plants are then regenerated from callus tissue by methods similar to those previously used by A. V. P. Dos Santos et al. (1980) Z. Pflanzenphysiol. 99:261–270; T. J. McCoy and E. T. Bingham (1977) Plant Sci. Letters 10:59–66; and K. A. Walker eta. (1979) Plant Sci. Letters 16:23–30. These regenerated plants are then propagated by conventional plant breeding techniques forming the basis for new commercial varieties.

Example 12

In all Examples, RNA was extracted, fractionated, and detected by the following procedures.

12.1 RNA extraction

This procedure was a modification of Silflow et al. (1981) Biochemistry 13:2725–2731. Substitution of LiCl precipitation for CsCl centrifugation was described by Murray et al. (1981) J. Mol. Evol. 17:31–42. Use of 2M LiCl plus 2M urea to precipitate was taken from Rhodes (1975) J. Biol. Chem. 25:8088–8097.

Tissue was homogenized using a polytron or ground glass homogenizer in 4–5 volumes of cold 50 mM Tris-HCl (pH8.0) containing 4% p-amino salicylic acid, 1% tri-isopropyl napthalene sulfonic acid, 10 mM dithiothreitol (freshly made) and 10 mM Na-metabisulfite (freshly made). An octanol was used as needed to control foaming. An equal volume of Tris-saturated phenol containing 1% 8-hydroxyquinoline was added to the homogenate which was then shaken to emulsify and centrifuged at 20,000–30,000 g for 15 minutes at 4° C. The aqueous upper phase was extracted once with chloroform/octanol (24:1) and centrifuged as above. Concentrated LiCl-urea solution was then added to a final concentration of 2M each and the mixture was left to stand at 20° C. for several hours. The RNA precipitate was then centrifuged down and washed with 2M liCl to disperse the pellet. The precipitate was then washed with 70% ethanol-0.3M Na-acetate and dissolved in sufficient sterile water to give a clear solution. One half volume of ethanol was added and the mixture put on ice for ½ hour, after which it was centrifuged to remove miscellaneous polysaccharides. The RNA precipitate was then recovered and redissolved in water or in sterile no salt poly(U) buffer.

12.2 Poly(U) Sephadex chromotography

Two poly-u Sephadex (trademark: Pharmacia, Inc., Uppsala, Sweden) buffers were used; the first with no salt containing 20 mM Tris, 1 mM EDTA and 0.1% SDS, and the second with 0.1M NaCl added to the first. In order to obtain a good match at $A_{260}$, a 2x stock buffer should be made and the salt added to a portion. After adjusting the final concentrations, the buffers are autoclaved.

Poly(U) Sephadex was obtained from Bethesda Research laboratories and 1 gm poly(U) Sephadex was used per 100 µg expected poly(A) RNA. The poly(U) Sephadex was hydrated in no salt poly(U) buffer and poured into a jacketed column. The temperature was raised to 60° C. and the column was washed with no salt buffer until the baseline at 260 mm was flat. Finally the column was equilibrated with the salt containing poly(U) buffer at 40° C. The RNA at a concentration of less than 500 µg/ml was then heated in no salt buffer at 65° C. for 5 minutes, after which it was cooled on ice and NaCl added to a concentration of 0.1M. The RNA was then placed on the column which was run at no more than 1 ml/min until the optical density had fallen to a steady baseline. The column temperature was then raised to 60° C. and the RNA was eluted with no salt poly(U) buffer. The RNA usually washed off in three column volumes. The eluted RNA was then concentrated with secondary butanol to a convenient volume after addition of NaCl to 10 mM, and precipitated with 2 volumes ethanol. The ethanol precipitate was dissolved in water and $NH_4$-acetate added to 0.1M, followed by re-precipitation with ethanol. Finally the RNA was redissolved in sterile water and stored at −70° C.

12.3 Formaldehyde RNA gel s and "Northern" blots

The method used followed that of Thomas (1980) Proc. Nat. Acad. Sci. USA 77:5201, and Hoffman, et al. (1981) J. Biol. Chem. 256:2597.

0.75–1.5% agarose gels containing 20 mM Na-phosphate (pH 6.8–7.0) were cast. If high molecular weight aggregate bands appeared, then the experiments were repeated with the addition of 6% or 2.2M formaldehyde (use stock solution of 36%) to the gels. The formaldehyde caused visualization with ethidium bromide to be very difficult. The running buffer was 10mM Na-phosphate (pH 6.8–7.0).

Prior to electrophoresis, the RNA was treated with a denaturing buffer having final concentrations of 6% formaldehyde, 50% formamide, 20 mM Na-phosphate buffer and 5 mM EDTA. The RNA was incubated in the buffer at 60° C. for 10–20 minutes. The incubation was terminated by addition of stop buffer. For a 20 µl sample, 4 µl 50% glycerol, 10 mM EDTA, 5 mM Na-phosphate and bromphenol blue were added.

Submerged electrophoresis was used. The RNA was loaded before the gel was submerged, and run into the gel at 125 mA for 5 minutes. The gels were then submerged and the current reduced to 30 mA (overnight) or 50 mA (6–8 hours). The buffer was recirculated and the electrophoresis was done in a cold room.

12.4 "Northern" blots

If the gel was to be blotted to detect a specific RNA, it was not stained; a separate marker lane was used for staining. Staining was with 5 µg/ml ethidium bromide in 0.1M Na-acetate and destaining was for several hours in 0.1M Na-acetate. Treatment in water at 60°–70° C. for 5–10 minutes prior to staining helped visualization.

A gel to be blotted was soaked for 15 minutes in 10x standard saline citrate (SSC)-3% formaldehyde. If large RNA molecules were not eluting from the gel then a prior treatment in 50 mM NaOH for 10–30 minutes helped to nick the RNA. If base treatment was used, the gel was neutralized and soaked in SSC-formaldehyde before blotting. Transfer of the RNA to nitrocellulose was done by standard methods.

Prehybridization was done at 42° C. for a minimum of 4 hours in 50% formamide, 10% dextran sulfate, 5x SSC, 5x Denhardt's, 100 µg/ml denatured carrier DNA, 20 µg/ml poly(A), 40mM Na-phosphate (pH 6.8–7.0) and 0.2% SDS. Hybridization was done by addition of the probe to the same buffer with overnight incubation. The probe was not used at more than approximately $5 \times 10^5$ cpm/ml.

After hybridization, the nitrocellulose was washed a number of times at 42° C. with 2x SSC, 25 mM Na-phosphate, 5 mM EDTA and 2 mM Na-pyrophosphate followed by a final wash for 20 minutes at 64° C. in 1x SSC. Best results were obtained if the filter was not dried prior to autoradiography and the probe could be removed by extensive washing in 1 mM EDTA at 64° C.

Example 13

"Western" blots, to detect antigens after SDS-polyacryl amide gel electrophoresis, were done essentially as described by R. P. Legocki and D. P. S. Verma (1981) Analyt. Biochem. 111:385–392.

Micro-ELISA (enzyme-linked immuno-sorbant assay) assays were done using Immulon-2 type plates with 96 wells by the following steps:

13.1 Binding antibody to plates

On Day 1, the wells were coated with 1:1000 dilution of antibody (rabbit antiphaseolin IgG) in coating buffer. 200 µl/well incubated at 37° C. for 2–4 hours. The plates were covered with Saran Wrap. Then the plates were rinsed three times with phosphate buffered saline-Tween (PBS-Tween) allowing a 5 minute waiting period between each rinse step. Then 1% bovine serum albumin (BSA) was added to rinse and, after addition to the well, left to sit for 20 minutes before discarding. Rinsing was repeated five times more with PBS-Tween.

13.2 Tissue homogenization

The tissue was sliced up into small pieces and then homogenized with a polytron using 1 gm of tissue/ml phosphate buffered saline-Tween-2% polyvinyl pyrolidone-40 (PBS-Tween-2% PVP-40). All samples were kept on ice before and after grinding and standard phaseolin curves were obtained. One standard curve was done in tissue homogenates and one standard curve was also done in buffer to check the recovery of phaseolin when ground in tissue. Following centrifugation of the homogenized samples, 100 µl of each sample was placed in a well and left overnight at 4° C. To avoid errors, duplicates of each sample were done. The plates were sealed during incubation.

13.3 Binding enzyme

After the overnight incubation, the antigen was discarded and the wells were washed five times with PBS-Tween allowing 5 minutes between each rinse.

A conjugate (rabbit anti-phaseolin IgG alkaline phosphatase linked) was then diluted 1:3000 in PBS-Tween-2% PVP containing 0.2% BSA and 150 µl was added to each well; followed by incubation for 3–6 hours at 37° C. After the incubation, the conjugate was discarded and the wells were rinsed five times with PBS-Tween, allowing five minutes between each rinse as before.

13.4 Assay

Immediately before running the assay, a 5 mg tablet of p-nitrophenyl phosphate (obtained from Sigma and stored frozen in the dark) was added per 10 ml substrate and vortexed until the tablet was dissolved. 200 µl of the room temperature solution was quickly added to each well. The reaction was measured at various times, e.g. t=0, 10, 20, 40, 60, 90 and 120 minutes, using a Dynatech Micro-ELISA reader. When p-nitrophenyl phosphate, which is colorless, was hydrolysed by alkaline phosphatase to inorganic phosphate and p-nitrophenol, the latter compound gave the solution a yellow color, which could be spectrophotometrically read at 410 nm. The lower limit of detection was less than 0.1 ng.

Example 14

Triparental matings were generally accomplished as described below; other variations known to those skilled in the art are also acceptable. E. coli K802 (pRK290-based shuttle vector) was mated with E. coli. (pRK2013) and an A. tumefaciens strain resistant to streptomycin. The pRK2013 transferred to the shuttle vector carrying strain and mobilized the shuttle vector for transfer to the Agrobacterium. Growth on a medium containing both streptomycin and the drug to which the shuttle vector is resistant, often either kanamycin or chloramphenicol, resulted in the selection of Agrobacterium cells containing shuttle vector sequences. A mating of these cells with E. coli (pPH1J1) resulted in the transfer of pPH1J1 to the Agrobacterium cells. pPH1J1 and pRK290-based shuttle vectors cannot coexist for long in the same cell. Growth on gentamycin, to which pPH1J1 carries a resistance gene, resulted in selection of cells having lost the pRK290 sequences. The only cells resistant to streptomycin, gentamycin, and either kanamycin or chloramphenicol are those which have Ti plasmids that have undergone double homologous recombination with the shuttle vector and now carry the desired construction.

Example 15

Regeneration of transformed tobacco plants and production of first generation tobacco seeds. Tissue of tobacco cultivar "Xanthi" 539-5 was transformed by infection with Agrobacteria containing a phaseolin gene inserted into the tml gene of Ti-plasmid pTiA66 (see Example 1.4) as described in Example 10.1. Clones were obtained from the transformed tissue as described in Example 10.2 with the following modifications. Calli were converted into cell suspensions by culturing in liquid MS containing 0.02 mg/l naphthalene acetic acid (NAA) and 0.2 mg/ml carbenicillin at 25° C. for 8 days while being shaken in the light at 110 rpm. The cell suspension was then filtered successively through 520 and 230 µm stainless steel meshes and the cell suspension was concentrated.

Aliquots of the cell suspension were grown on feeder plates made as follows: 30 ml MS medium+0.5 mg/l NAA+ untransformed tobacco cells in 0.8% agar were added to each plate and covered with filter paper. A second filter was placed on the first filter paper and aliquots of the transformed cells were spotted onto this second filter paper. Three clones were recovered and these developed into calli. Pieces of these calli were transferred into 125 ml flasks containing MS medium (without hormones) plus 0.5 mg/ml carbenicillin. When shoots had developed, grafts onto tobacco plants were carried out as follows. Firstly, the tobacco plant was cross-sectioned at a node and a cut was made across the stem to a depth of about 1.5 cm. The transformed shoot was then trimmed by removal of the lower leaves and the stem was cut at a long angle. The shoot was then placed in the cut of the root stock with the angled side towards the center. The graft was held in place by wrapping elastic sticky tape around the sides, thus holding the grafted shoot tightly. The top of the cut stem was also wrapped. A plastic bag was then laced over the grafted shoot and the cut stem and some holes were punched in the bag. The bag was removed after seven days and the intensity of light gradually increased to normal growing conditions. The grafted shoots developed into normal tobacco plants and an abundant seed set was obtained. These seeds are herein defined as first generation tobacco seeds.

Example 16

Demonstration of presence of phaseolin in first generation seeds of regenerated, transformed tobacco plants. Initially, batches of approximately 100 transformed first generation tobacco seeds were ground in a mortar and pestle and the proteins were analyzed by "Western" blots and by "micro-ELISA" assays. Substantial amounts of phaseolin were detected as well as a number of characteristic degradation products. These are a number of genes controlling the synthesis of three phaseolin types in bean plants; the phaseolin types are designated α, β, and gamma. The β-phaseolin of bean was expressed here in the tobacco seeds.

In further tests, individual seeds were ground and tested as above for the presence of β-phaseolin and its characteristic degradation products. Seventy-five percent of the seeds contained β-phaseolin and the degradation products. Since the seeds were obtained by selfing, this is the results that would be expected from self-fertilization of a plant heterozygous for a dominant gene, i.e. 25% seeds homozygous for the transferred phaseolin gene; 50% heterozygous for the transferred phaseolin gene and 25% without any transferred phaseolin gene.

Finally, individual seeds were dissected into embryo and endosperm and the above mentioned tests (i.e. Western blots) were carried out to detect the tissue specificity of phaseolin. In all seeds where phaseolin was present, it was found in both the endosperm and the embryo.

The phaseolin content of individual seeds ranged from 0.6% to 3.4% of the total seed protein. It must be noted that this amount of phaseolin is the product of a single gene and that amplification of this gene can lead to greatly increased yields.

Example 17: Synthesis of phaseolin in tobacco seeds and post-transcriptional processing of phaseolin gene products in tobacco seeds There are three forms of phaseolin (α, β and γ) normally found in bean seeds. They have molecular weights of 51 kD, 48 kD and 45.5 kD, respectively. The β-form has been transferred to tobacco plants and seeds have been obtained from these plants. β-phaseolin was present in the transformed tobacco seeds as shown by the following evidence. Initially, ELISA tests showed the presence of immunoreactive proteins in the seeds, Subsequently the presence of phaseolin was demonstrated by standard Western blot procedures. In addition to the full length protein of 48 kd, immunoreaction was seen with several discrete bands with molecular weights in the region of 20 to 25 kD. These same bands were also found when phaseol in was extracted from bean seeds and examined by the same Western blot methods, thus indicating that phaseolin is processed in the same way regardless of whether it is in the natural habitat (i.e., the bean seed) or in an engineered habitat (i.e., the tobacco seed).

Further evidence of normal post-translational processing was obtained from glycosylation studies. Phaseolin, like other glycoproteins, undergoes post-translational glycosylation. Because of a high mannose content, phaseolin binds to Concannavalin A. To test for glycosylation, samples of total protein from control and transformed tobacco seeds were incubated with Concanavalin A (ConA) for several hours. Then the ConA was washed followed by removal of any bound protein by sodium dodecyl sulfate (SDS). The eluted proteins were then subjected to electrophoresis and subsequently Western blot hybridization as usual. Results showed that proteins co-migrating with authentic phaseol in were glycosylated and that one of the lower weight degradation products also bound mannose residues.

Further experiments were then done with transformed tobacco seeds to demonstrate that phaseolin protein is processed like a normal seed protein. Transformed tobacco seeds were sterilized and placed on sterile agar plates for periods ranging from 1 day to 5 days. The proteins from the germinating seeds (1d, 2d, 3d, 4d and 5d) were extracted and subjected to sodium dodecyl sulfate-polyacrylamide gel electrophoresis followed by Western blotting using anti-phaseol in antibody.

As stated above, phaseolin in tobacco seeds migrated partly as the authentic size protein while the major fraction migrated as discrete bands in the molecular weight range between 20 kD to 25 kD. During germination the authentic size phaseolin was gradually degraded to the lower molecular weight protein until, 5 days after germination when the seeds had developed into little seedlings, there was no trace of phaseolin in the tissues.

Phaseolin is a seed protein and as such should only be present in the seeds. Normally during germination, phaseolin in beans is degraded and used by the growing seedling. The fact that phaseolin was similarly degraded in germinating tobacco seeds showed that the phaseolin gene product was tissue specific both with respect to location and function. In addition, during germination, the authentic size phaseolin was degraded with a concommitant increase in the lower molecular weight protein. Most significantly, phaseolin was made and properly processed in tobacco seeds. However, the small seeds of tobacco lacked the capacity of bean seeds for storing phaseolin so more of the phaseolin "overflowed" the storage capacity of the tobacco seeds and was degraded to the smaller sized proteins.

Example 18

Germination of first generation tobacco seeds and grafting of second generation seedlings onto tobacco plants and tomato plants.

First generation tobacco seeds were germinated on MS medium and grown in the light. Twenty-five percent of these seeds grew tall, produced normal leaves, and were phenotypically normal. These plants contained untransformed cells. The plants derived from the remaining 75% of seeds were stunted and the cotyledons were small and dark green. These stunted seedlings contain transformed cells and developed from seeds containing phaseolin (determined by Western blots and micro-ELISA assays). Tests of the genomic DNA of these stunted seedlings by Southern blots established the presence of the bean β-phaseolin gene.

In order to obtain whole plants from these stunted seedlings, it was necessary to graft them onto normal root stocks. Eight-week old tobacco plants of cultivar "Xanthi" were used as root stocks in some instance while tomato plants were used as root stocks in other instances.

Before grafting, the stunted plants were treated as follows: 25–30 ml liquid MS medium was added to a Petri plate and a 520 μm screen was placed over the top of the plate. The stunted seedlings were rested on the edges in such a manner that the root stubs were in the liquid while the rest of the plant was above the liquid. The plants were then incubated in the light for eight days at 34 C after which period the stems had enlarged to the extent that it was possible to carry out the grafting onto tobacco and tomato root stocks. Grafts of these seedlings were made into various nodal positions on the tobacco and tomato root stocks. The majority of the grafted seedlings grew into normal plants and large numbers of seeds were obtained after self fertilization of each transformed plant. The seeds from each plants were stored separately and such seeds are herein defined as second generation seeds. Furthermore, plants grown from these second generation seeds are defined herein as second generation plants and the component parts of these second generation plants are defined as second generation plant tissue.

Example 19

Demonstration of the presence of phaseolin in second generation plant tissue and second generation seeds.

Initially, small batches of second generation seeds were ground in a mortar and pestle and analyzed by Western blotting. β-phaseolin and the specific degradation products were present in all the samples.

Individual seeds obtained by self fertilization of individual plants were then analyzed in the same manner. In several instances, all the seeds from an individual plant contained phaseolin and its specific degradation products indicating that the genome was homozygous for the phaseolin gene inserted into the incorporated T-DNA. In other instances, 75% of the seeds contained β-phaseolin and its degradation products indicating that the genome was heterozygous for the phaseol in gene inserted into the incorporated DNA (as was the case for the first generation seeds of regenerated, transformed tobacco plants, see Example 16).

Seeds of tobacco containing and expressing the phaseolin gene as described herein (Strain: Tobean) are on deposit at Agrigenetics Advanced Research Division, 5649 East Buckeye Road, Madison, Wis. 53716. Access to the material on deposit will be available during the pending period of the patent application to one determined by the Commissioner to be entitled thereto under 37 C.f.r. 1.14 and 35 USC 122, and all restrictions on availability to the public of the materials so deposited will be irrevocably removed upon the granting of the patent.

The materials on deposit or viable replications thereof shall be maintained on deposit at the above given address for the life of the patent.

We claim:

1. A plasmid selected from the group consisting of pKS-OS-KB3.0, pKS-nopIV-KB3.8#3, pKS-nopIVK3.8#5, p499/6/7, p499/6/8, p490/6/2, p490/6/1, p395, p376, pKS4, p3.8, and pcDNA 31.

2. A bacterial strain selected from the group consisting of *A. tumefaciens*/p529-2, *A. tumefacien*/p529/8, *A. tumefaciens*/p539-5, *A. tumefaciens*/pC58-nop-KS#3, *A. tumefaciens*/p58-nop-KB#5, *E. coli* K802/pKS-OS-KB3.0, *E. coli* K802/pKS-nopIV-KB3.8#3, *E. coli* K802/pKS-nopIV-KB3.8#5, *A. tumefaciens*/p529-11, *E. coli* K802/p499/6/7, *E. coli* K802/p499/6/8, *E. coli* K802/p496-2, *E. coli* K802/p496-1, *E. coli* K802/p490-8/14, and *e. coli* K802/p458-8.

3. A bacterial strain comprising a plasmid of claim 1.

4. Plant tissue of a dicotyledonous plant comprising a genetically modified plant cell selected from the group consisting of:

a) transformable plant cells wherein a phaseolin structural gene and promoter have been introduced into said plant cell via T-DNA, and wherein said introduced phaseolin structural gene is expressed in said plant cell, and b) progeny cells of said plant cell of paragraph a) containing and expressing said gene.

5. Plant tissue according to claim 4 wherein the phaseolin gene is inserted in tml.

6. A bacterial strain selected from the group consisting of *Agrobacterium tumefaciens* and *Agrobacterium rhizogenes*, comprising a TIP plasmid selected from the group consisting of p529-2, p529-8, p539-9, pC58-nop-KB#3, and pC58-nop-KB#5.

7. An isolated DNA molecule comprising the phaseolin promoter.

8. An isolated DNA molecule of claim 7, wherein said molecule comprises the 3.8 kbp fragment from an EcoRI site to the BamHI site in pKS-KB3.8.

9. The isolated DNA molecule of claim 7 wherein said molecule comprises the 3.0 kbp fragment from an EcoRI site through the BamHI site of pKS4-KB.

10. The isolated DNA molecule of claim 7, wherein said molecule comprises a 1308 base pair fragment from an EcoRI site through a SacI site resulting from complete EcoRI digest and partial SacI digest of pCDNA31.

11. A dicot plant ell comprising a heterologous plant promoter that controls the expression of a gene in said plant cell, wherein said heterologous plant promoter is a phaseolin promoter.

12. Progeny of the cell of claim 11.

13. Dicot plant tissue comprising a cell according to claim 11.

14. The dicot plant tissue of claim 13, wherein said tissue is a seed.

15. A whole transformed dicot comprising a cell according to claim 11.

16. A dicot plant cell comprising a heterologous plant promoter that controls the expression of a gene in said plant cell, wherein said heterologous plant promoter is a phaseolin promoter, wherein said cell comprises the 3.8 kps fragment from an EcoRI site through the BamHI site of pKS4-KB.

17. Progeny of the cell of claim 16.

18. Dicot plant tissue comprising a cell according to claim 16.

19. The dicot plant tissue of claim 18, wherein said tissue is a seed.

20. A whole transformed dicot comprising a cell according to claim 16.

21. A dicot plant cell comprising a heterologous plant promoter that controls the expression of a gene in said plant cell, wherein said heterologous plant promoter is a phaseolin promoter, wherein said cell comprises the 3.0 kbp fragment from an EcoRI site through the BamHI site of pKS4-KB.

22. Progeny of the cell of claim 21.

23. Dicot plant tissue comprising a cell according to claim 21.

24. The dicot plant tissue of claim 23, wherein said tissue is a seed.

25. A whole transformed dicot comprising a cell according to claim 21.

26. A dicot plant cell comprising a heterologous plant promoter that controls the expression of a gene in said plant cell, wherein said heterologous plant promoter is a phaseolin promoter, wherein said cell comprises a 1308 base pair fragment from an EcoRI site through a SacI site resulting from complete EcoRI digest and partial SacI digest of pCDNA31.

27. Progeny of the cell of claim 26.

28. Dicot plant tissue comprising a cell according to claim 26.

29. The dicot plant tissue of claim 28, wherein said tissue is a seed.

30. A whole transformed dicot comprising a cell according to claim 26.

* * * * *

UNITED STATES PATENT AND TRADEMARK OFFICE
CERTIFICATE OF CORRECTION

PATENT NO. : 5,504,200
DATED : April 2, 1996
INVENTOR(S) : Hall et al.

It is certified that error appears in the above-indentified patent and that said Letters Patent is hereby corrected as shown below:

Abstract: Line 1: "disposed." should read --disclosed.--

Column 3: Line 14: "166: 357-384" should read --16: 357-384--; Line 18: "transformed in by Agrobacterium a number" should read --transformed by Agrobacterium in a number--.

Column 7: Line 31: "799: 3193-3197" should read --79: 3193-3197--.

Column 8: Line 11: "et al. supra)." should read --et al., supra).-- .

Column 9: Line 9: "Syrup." should read --Symp.--; Line 46 "Sinai" should read --SmaI--; Line 55: "Phaseol in" should read --Phaseolin--.

Column 10: Line 11: "phaseol in" should read --phaseolin--.

Column 11: Line 16: "pKS-oct. delI" should read --pKS-oct.delI--; Line 17: "p2f-rt/p103-1 ft" should read --p2f-rt/p103-1ft--; Line 29: "inear" should read --linear--; Line 52: "FIG. 23 depicts plasmid construction of plasmid construct p2f." should read --FIG. 23 depicts the construction of plasmid construct p2f.--.

Column 12: Line 2: "pressure" should read --presence--; Line 24: "al)" should read --all--.

UNITED STATES PATENT AND TRADEMARK OFFICE
CERTIFICATE OF CORRECTION

PATENT NO.  : 5,504,200
DATED       : April 2, 1996
INVENTOR(S) : Hall et al.

Page 2 of 4

It is certified that error appears in the above-indentified patent and that said Letters Patent is hereby corrected as shown below:

Column 16: Line 38: "phaseol in" should read --phaseolin--; Line 48: "phaseol in" should read --phaseolin--;

Column 18: Line 7: "nopIV-KB3.8A5" should read nopIV-KB3.8Δ5--; Line 10: "12.3" should read --2.3--; Line 38: "Slightore" should read --Slightom--; Line 47: "AGpPVPh3.8" should read --AG-pPVPh3.8--; Line 48: "BB1II" should read --Bg1II--.

Column 19: Line 3: "phaseol in" should read --phaseolin--.

UNITED STATES PATENT AND TRADEMARK OFFICE
CERTIFICATE OF CORRECTION

PATENT NO. : 5,504,200  
DATED : April 2, 1996  
INVENTOR(S) : Hall et al

Page 3 of 4

It is certified that error appears in the above-indentified patent and that said Letters Patent is hereby corrected as shown below:

Column 22: Line 6: "BgIII" should read --BgII--; Line 10: "clone" should read --clone (pKS-oct.delIIIa)--; Line 11: "BgIIII" should read --BgIII--; Line 23: "H.paI" should read --HpaI--; Line 45: "Ribased" should read --Ri-based--.

Column 23: Line 33: "interval s" should read --intervals--; Line 42: "naphtalene" should read --naphthalene--; Line 44: "213 $\mu$um" should read --213 $\mu$m--; Line 48: "cells/mi." should read --cells/ml.--.

Column 24: Line 21: "phaseol in" should read --phaseolin--; Line 39: "pti15955" should read --pTi15955--; Line 57: "Walker eta." should read --Walker et al.--.

Column 25: Line 59: "gel s" should read --gels--.

Column 27: Line 4: "pyrolidone - 40" should read --pyrollidone - 40--.

Column 29: Line 23: "phaseol in" should read --phaseolin--; Line 39: "phaseol in" should read --phaseolin--; Line 50: "phaseol in" should read --phaseolin--.

Column 30: Line 66: "phaseol in" should read --phaseolin--.

UNITED STATES PATENT AND TRADEMARK OFFICE
CERTIFICATE OF CORRECTION

PATENT NO. : 5,504,200
DATED : April 2, 1996
INVENTOR(S) : Hall et al.

It is certified that error appears in the above-indentified patent and that said Letters Patent is hereby corrected as shown below:

Column 31: line 22, "tumefacien/p529/8" should read --tumefaciens/p529/8--; Line 23: "nop-KS#3," should read --nop-KB#3,--; Line 28: "p496-1," should read --p496-2,--; Line 37: "progency" should read --progeny--;

Column 32: Line 5: "plant ell" should read --plant cell--; Line 18: "3.8 kps" should read --3.8 kbp--; Line 20: "Progency" should read --Progeny-- line 32, "Progency" should read --Progeny-- line 46, "Progency" should read --Progeny--.

Signed and Sealed this

Fourth Day of November, 1997

BRUCE LEHMAN

Attest:

Attesting Officer

Commissioner of Patents and Trademarks